United States Patent
Palanivelu et al.

(10) Patent No.: US 7,109,149 B2
(45) Date of Patent: Sep. 19, 2006

(54) REGULATION OF PLANT FERTILITY BY MODULATION OF GABA LEVELS IN FLOWERS

(75) Inventors: Ravishankar Palanivelu, Tucson, AZ (US); Laura Brass, Newton, MA (US); Daphne Preuss, Chicago, IL (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 10/177,717

(22) Filed: Jun. 21, 2002

(65) Prior Publication Data

US 2004/0177398 A1 Sep. 9, 2004

Related U.S. Application Data

(60) Provisional application No. 60/300,513, filed on Jun. 22, 2001.

(51) Int. Cl.
  *A01N 37/44* (2006.01)
  *A01N 43/16* (2006.01)
  *A01N 43/28* (2006.01)
  *A01N 43/40* (2006.01)
  *A01P 21/00* (2006.01)

(52) U.S. Cl. ............... 504/244; 504/271; 504/275; 504/292; 504/320; 504/322; 504/326

(58) Field of Classification Search ............ 504/244, 504/271, 275, 292, 320, 322, 326
See application file for complete search history.

(56) References Cited

U.S. PATENT DOCUMENTS

| | | | |
|---|---|---|---|
| 4,936,904 A | 6/1990 | Carlson | ................ 71/94 |
| 5,439,873 A | 8/1995 | Kinnersley | |
| 6,075,051 A | 6/2000 | Cohen | |
| 6,268,206 B1 | 7/2001 | Liptak | |
| 6,534,446 B1* | 3/2003 | Kinnersley et al. | ......... 504/147 |

FOREIGN PATENT DOCUMENTS

WO  WO 00/61763  10/2000

OTHER PUBLICATIONS

Narayan et al. "Metabolism, enzymology and possible roles of 4-aminobutyrate in higher plants", Review Article No. 51, Phytochemistry. 29(2):367-375. 1990.*
Bown et al. "TheMetabolism and Functions of γ-Aminobutyric Acid" Update on Biochemistry. Plant Physiology. 115:1-5. 1997.*
Devlin, "The pharmacology of γ-aminobutyric acid and acetylcholine receptors at the echinoderm neuromuscular junction," *J Exp Biol.*, 204(Pt 5):887-896, 2001.
Enna, "Gaba receptor pharmacology. Functional considerations," *Biochem. Pharmacol.*, 30:907-915, 1981.
GenBank Accession No. AF351125.
Jefferson, "Benzodiazepines and anticonvulsants for social phobia (social anxiety disorder)," *J Clin Psychiatry.*, 62 Suppl 1:50-53, 2001.
Krysan et al., "T-DNA as an insertional mutagen in Arabidopsis," *Plant Cell*, 11(12):2283-2290, 1999.
Potschka et al., "Gabapentin-lactam, a close analogue of the anticonvulsant gabapentin, exerts convulsant activity in amygdala kindled rats," *Naunyn Schmiedebergs Arch Pharmacol.*, 361(2):200-205., 2000.
Schousboe, "Pharmacological and functional characterization of Astrocytic GABA transport: a short review," *Neurochem Res.*, 25(9-10):1241-1244, 2000.
Schwartz, "The $Gaba_A$ receptor-gated ion channel: biochemical and pharmacological studies of the structure and function," *Biochem. Pharmacol.*, 27:3369-3376, 1988.
Shelp et al., "Metabolism and function of gamma-aminobutyric acid," *Trends Plant Sci.*, 4(11):446-452, 1999.
Wilhelmi and Preuss, "Self-sterility in Arabidopsis due to defective pollen tube guidance," *Science.*, 274(5292):1535-1537, 1996.
Wilhelmi, In: *The Arabidopsis POP2 and POP3 Genes: Key Components in Pollen Tube Guidance*, Ph.D. thesis, The University of Chicago, 1999.
Database EMBL., May 15, 2001, Database accession No. AF351125.
Database GSP, Mar. 6, 2001, Database accession No. AAB19490.
Mascarenhas, Joseph P. "Molecular mechanisms of pollen tube growth and differentiation," *Plant Cell* vol. 5, No. 10, 1993, pp. 1303-1314.
Palanivelu, Ravishankar et al. "Pollen tube targeting and axon guidance: Parallels in tip growth mechanisms," *Trends in Cell Biology*, Vo. 10, No. 12, Dec. 2000, pp. 517-524.

* cited by examiner

*Primary Examiner*—S. Mark Clardy
(74) *Attorney, Agent, or Firm*—Woodard, Emhardt, Moriarty, McNett & Henry LLP

(57) ABSTRACT

The invention provides methods for the alteration of fertility in plants through modulation of floral GABA levels. The techniques of the invention may find use in plant breeding techniques. Also provided by the invention are assays for the screening of candidate modulators of GABA metabolism or GABA analogs through the identification of affects on fertility following application of the candidate modulator to a plant. The technique provides an alternative to animal testing and is amenable to large scale application.

13 Claims, 10 Drawing Sheets

Pollen tube guidance defects in *pop2*

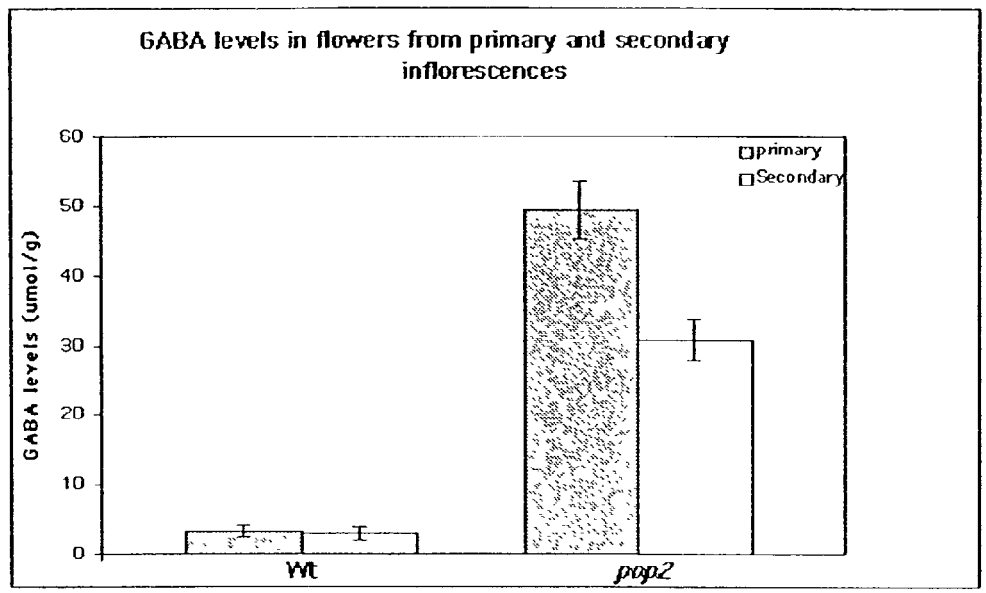
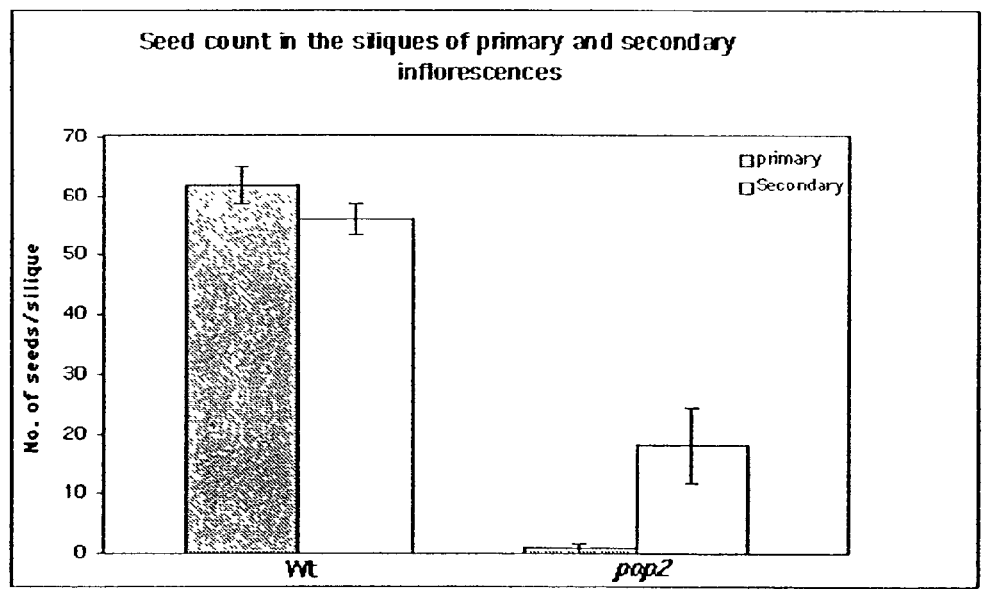
FIG. 6A-B

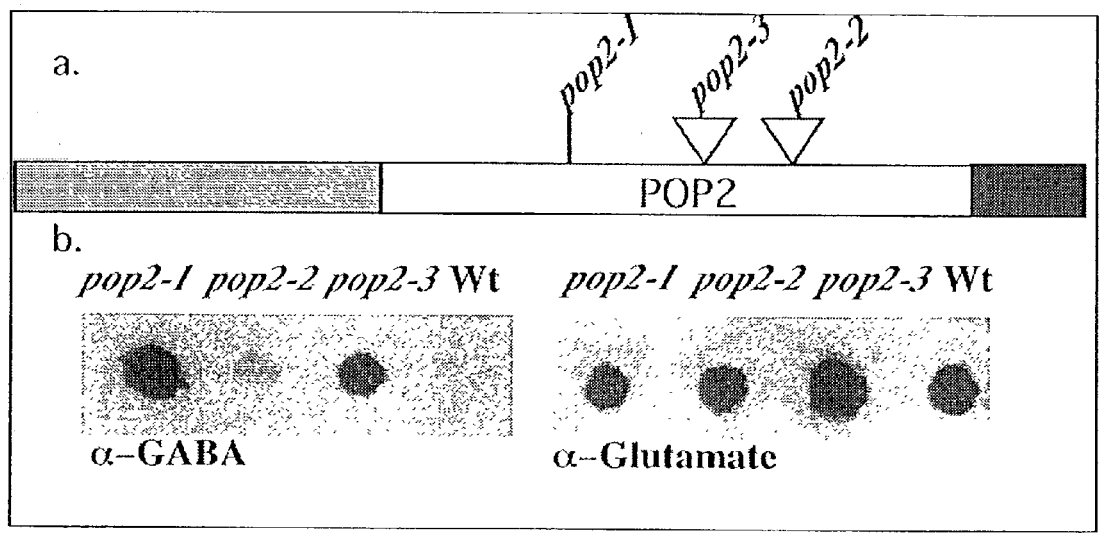
FIG. 7A-B

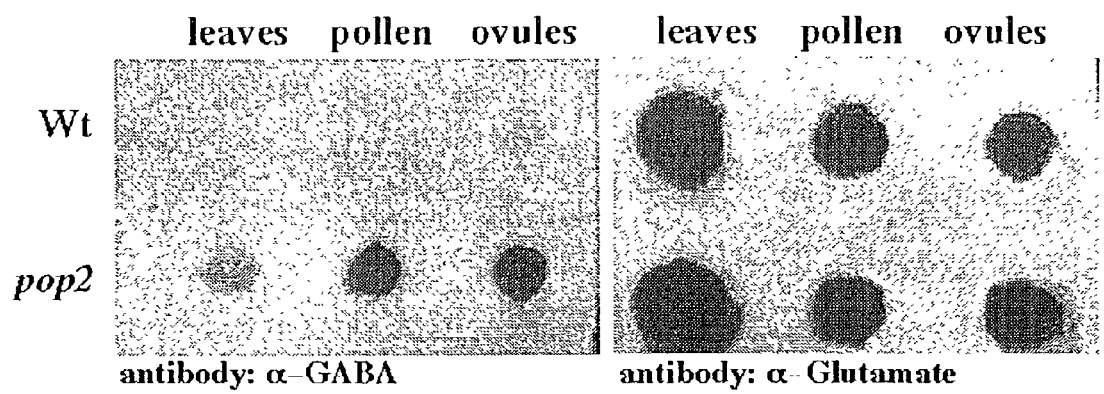
FIG. 8A-B

GABA Localization in pollinated wild type and *pop2* pistils

SEQUENCE LISTING

<160> NUMBER OF SEQ ID NOS: 2

<210> SEQ ID NO 1
<211> LENGTH: 1737
<212> TYPE: DNA
<213> ORGANISM: Arabidopsis thaliana
<220> FEATURE:
<221> NAME/KEY: CDS
<222> LOCATION: (103)..(1617)

<400> SEQUENCE: 1

```
agtgtgagta atttagatcc aggattcttc agattcctct cctttgatcc tctctttaac        60
aatctctctc tctctgtttt cttcgatccg ttgtaggaga aa atg gtc gtt atc          114
                                              Met Val Val Ile
                                                1 aac agt ctc cga cgc ttg gcg cgt acc act cag gtt cat ttg cac agt         162
Asn Ser Leu Arg Arg Leu Ala Arg Thr Thr Gln Val His Leu His Ser
  5                  10                  15                  20 agg tat gcc act tgc atg tct ggg aac tcc act tcc agg agg att ttc         210
Arg Tyr Ala Thr Cys Met Ser Gly Asn Ser Thr Ser Arg Arg Ile Phe
                 25                  30                  35 act act gag gca gca cct gag aag aaa aac act gtt ggg tct aaa ggg         258
Thr Thr Glu Ala Ala Pro Glu Lys Lys Asn Thr Val Gly Ser Lys Gly
             40                  45                  50 cat gat atg ctt gca cct ttt act gct gga tgg cag agt gct gat tta         306
His Asp Met Leu Ala Pro Phe Thr Ala Gly Trp Gln Ser Ala Asp Leu
         55                  60                  65 gat ccc ttg gtc att gca aag tct gag gga agt tat gtg tat gat gat         354
Asp Pro Leu Val Ile Ala Lys Ser Glu Gly Ser Tyr Val Tyr Asp Asp
     70                  75                  80 act ggg aaa aaa tat ctt gac tct ctc gct ggt tta tgg tgt act gcc         402
Thr Gly Lys Lys Tyr Leu Asp Ser Leu Ala Gly Leu Trp Cys Thr Ala
 85                  90                  95                 100 tta gga gga aat gag cca agg ctt gtt tct gcc gct gtt gaa cag ttg         450
Leu Gly Gly Asn Glu Pro Arg Leu Val Ser Ala Ala Val Glu Gln Leu
                105                 110                 115 aac acc ttg ccg ttt tat cac tcc ttt tgg aac cgt act act aaa cct         498
Asn Thr Leu Pro Phe Tyr His Ser Phe Trp Asn Arg Thr Thr Lys Pro
            120                 125                 130 tct ctg gat ctt gct aag gtt ctt tta gag atg ttc acg gcc aac aaa         546
Ser Leu Asp Leu Ala Lys Val Leu Leu Glu Met Phe Thr Ala Asn Lys
        135                 140                 145 atg gcc aaa gca ttt ttt aca agc ggt gga tca gat gcc aac gat acc         594
Met Ala Lys Ala Phe Phe Thr Ser Gly Gly Ser Asp Ala Asn Asp Thr
    150                 155                 160 cag gtc aag ctg gtt tgg tat tac aat aac gca ctt gga agg ccc gag         642
Gln Val Lys Leu Val Trp Tyr Tyr Asn Asn Ala Leu Gly Arg Pro Glu
165                 170                 175                 180 aag aaa aag ttt atc gcg aga aag aaa tcg tac cat ggc tcc act cta         690
Lys Lys Lys Phe Ile Ala Arg Lys Lys Ser Tyr His Gly Ser Thr Leu
                185                 190                 195 ata tca gca agt ttg tcc ggc ctt ccc ccg cta cac caa aat ttt gat         738
Ile Ser Ala Ser Leu Ser Gly Leu Pro Pro Leu His Gln Asn Phe Asp
            200                 205                 210 tta cct gca cca ttt gtg ttg cac aca gat tgc cct cat tat tgg cgt         786
Leu Pro Ala Pro Phe Val Leu His Thr Asp Cys Pro His Tyr Trp Arg
        215                 220                 225 ttt cat ctt cca ggc gaa acg gaa gag gag ttc tca acc aga tta gcc         834
Phe His Leu Pro Gly Glu Thr Glu Glu Glu Phe Ser Thr Arg Leu Ala
    230                 235                 240 aag aat tta gag gat cta atc atc aaa gaa gga cca gaa act att ggt         882
Lys Asn Leu Glu Asp Leu Ile Ile Lys Glu Gly Pro Glu Thr Ile Gly
245                 250                 255                 260 gct ttt ata gct gaa cca gtc atg ggt gct ggg ggt gtg ata cct cca         930
Ala Phe Ile Ala Glu Pro Val Met Gly Ala Gly Gly Val Ile Pro Pro
                265                 270                 275 cct gct acc tac ttt gaa aag gtt caa gct gtt gtt aag aaa tat gat         978
Pro Ala Thr Tyr Phe Glu Lys Val Gln Ala Val Val Lys Lys Tyr Asp
```

-continued

```
                              280                 285                 290
atc ttg ttc att gct gat gag gtg ata tgt gca ttt gga agg ctc ggg         1026
Ile Leu Phe Ile Ala Asp Glu Val Ile Cys Ala Phe Gly Arg Leu Gly
            295                 300                 305 aca atg ttt ggc tgt gac aaa tac aac att aag cca gat ctt gtg acc         1074
Thr Met Phe Gly Cys Asp Lys Tyr Asn Ile Lys Pro Asp Leu Val Thr
    310                 315                 320 tta gct aag gca ctg tct tca gca tat atg ccg att gga gcc att ctt         1122
Leu Ala Lys Ala Leu Ser Ser Ala Tyr Met Pro Ile Gly Ala Ile Leu
325                 330                 335                 340 atg agc caa gaa gtg gca gat gtc ata aat tct cat agc agc aag ctt         1170
Met Ser Gln Glu Val Ala Asp Val Ile Asn Ser His Ser Ser Lys Leu
                345                 350                 355 ggc gtt ttc tcc cat gga ttt act tat tct ggt cat cca gtt tcg tgt         1218
Gly Val Phe Ser His Gly Phe Thr Tyr Ser Gly His Pro Val Ser Cys
            360                 365                 370 gct gta gca att gaa gcg tta aag ata tac aag gag agg aac ata cca         1266
Ala Val Ala Ile Glu Ala Leu Lys Ile Tyr Lys Glu Arg Asn Ile Pro
    375                 380                 385 gag tat gtc gcc aaa gtt gcc cca agg ttt caa gat gga gtt aaa gcg         1314
Glu Tyr Val Ala Lys Val Ala Pro Arg Phe Gln Asp Gly Val Lys Ala
390                 395                 400 ttt gcc tct ggt agt cct att att gga gag aca aga gga aca ggt ttg         1362
Phe Ala Ser Gly Ser Pro Ile Ile Gly Glu Thr Arg Gly Thr Gly Leu
405                 410                 415                 420 att ctt ggg act gag ttt gta gac aat aaa tct ccg aac gaa cca ttt         1410
Ile Leu Gly Thr Glu Phe Val Asp Asn Lys Ser Pro Asn Glu Pro Phe
                425                 430                 435 cca cca gaa tgg ggt gtt ggc gca ttc ttt gga gcc gag tgc cag aag         1458
Pro Pro Glu Trp Gly Val Gly Ala Phe Phe Gly Ala Glu Cys Gln Lys
            440                 445                 450 cac ggg atg tta gtc cgt gtt gca ggt gat ggc att ttg atg tct cca         1506
His Gly Met Leu Val Arg Val Ala Gly Asp Gly Ile Leu Met Ser Pro
    455                 460                 465 ccg ctc att atc tca cct gaa gag att gat gag ttg att tct atc tat         1554
Pro Leu Ile Ile Ser Pro Glu Glu Ile Asp Glu Leu Ile Ser Ile Tyr
470                 475                 480 ggg aaa gca ttg aag gca acg gaa gag aag gta aaa gaa ctc aag gct         1602
Gly Lys Ala Leu Lys Ala Thr Glu Glu Lys Val Lys Glu Leu Lys Ala
485                 490                 495                 500 cag cac aag aag tga aaagcagagt caaaatgatg ttgatgaaaa atgtttttta         1657
Gln His Lys Lys
                505 gattctcaaa gtttggatct attgtttttt tttttaacac acaacaagtc tttaaataag       1717 tacaaaaaaa aaaaaaaaa                                                    1737

<210> SEQ ID NO 2
<211> LENGTH: 504
<212> TYPE: PRT
<213> ORGANISM: Arabidopsis thaliana

<400> SEQUENCE: 2

Met Val Val Ile Asn Ser Leu Arg Arg Leu Ala Arg Thr Thr Gln Val
 1               5                  10                  15

His Leu His Ser Arg Tyr Ala Thr Cys Met Ser Gly Asn Ser Thr Ser
                20                  25                  30

Arg Arg Ile Phe Thr Thr Glu Ala Ala Pro Glu Lys Lys Asn Thr Val
        35                  40                  45
```

-continued

```
Gly Ser Lys Gly His Asp Met Leu Ala Pro Phe Thr Ala Gly Trp Gln
 50                  55                  60

Ser Ala Asp Leu Asp Pro Leu Val Ile Ala Lys Ser Glu Gly Ser Tyr
 65                  70                  75                  80

Val Tyr Asp Asp Thr Gly Lys Lys Tyr Leu Asp Ser Leu Ala Gly Leu
                 85                  90                  95

Trp Cys Thr Ala Leu Gly Gly Asn Glu Pro Arg Leu Val Ser Ala Ala
            100                 105                 110

Val Glu Gln Leu Asn Thr Leu Pro Phe Tyr His Ser Phe Trp Asn Arg
        115                 120                 125

Thr Thr Lys Pro Ser Leu Asp Leu Ala Lys Val Leu Leu Glu Met Phe
130                 135                 140

Thr Ala Asn Lys Met Ala Lys Ala Phe Phe Thr Ser Gly Gly Ser Asp
145                 150                 155                 160

Ala Asn Asp Thr Gln Val Lys Leu Val Trp Tyr Tyr Asn Asn Ala Leu
                165                 170                 175

Gly Arg Pro Glu Lys Lys Phe Ile Ala Arg Lys Lys Ser Tyr His
            180                 185                 190

Gly Ser Thr Leu Ile Ser Ala Ser Leu Ser Gly Leu Pro Pro Leu His
        195                 200                 205

Gln Asn Phe Asp Leu Pro Ala Pro Phe Val Leu His Thr Asp Cys Pro
210                 215                 220

His Tyr Trp Arg Phe His Leu Pro Gly Glu Thr Glu Glu Phe Ser
225                 230                 235                 240

Thr Arg Leu Ala Lys Asn Leu Glu Asp Leu Ile Lys Glu Gly Pro
                245                 250                 255

Glu Thr Ile Gly Ala Phe Ile Ala Glu Pro Val Met Gly Ala Gly Gly
            260                 265                 270

Val Ile Pro Pro Ala Thr Tyr Phe Glu Lys Val Gln Ala Val Val
        275                 280                 285

Lys Lys Tyr Asp Ile Leu Phe Ile Ala Asp Glu Val Ile Cys Ala Phe
290                 295                 300

Gly Arg Leu Gly Thr Met Phe Gly Cys Asp Lys Tyr Asn Ile Lys Pro
305                 310                 315                 320

Asp Leu Val Thr Leu Ala Lys Ala Leu Ser Ser Ala Tyr Met Pro Ile
                325                 330                 335

Gly Ala Ile Leu Met Ser Gln Glu Val Ala Asp Val Ile Asn Ser His
            340                 345                 350

Ser Ser Lys Leu Gly Val Phe Ser His Gly Phe Thr Tyr Ser Gly His
        355                 360                 365

Pro Val Ser Cys Ala Val Ala Ile Glu Ala Leu Lys Ile Tyr Lys Glu
370                 375                 380

Arg Asn Ile Pro Glu Tyr Val Ala Lys Val Ala Pro Arg Phe Gln Asp
385                 390                 395                 400

Gly Val Lys Ala Phe Ala Ser Gly Ser Pro Ile Ile Gly Glu Thr Arg
                405                 410                 415

Gly Thr Gly Leu Ile Leu Gly Thr Glu Phe Val Asp Asn Lys Ser Pro
            420                 425                 430

Asn Glu Pro Phe Pro Pro Glu Trp Gly Val Gly Ala Phe Phe Gly Ala
        435                 440                 445

Glu Cys Gln Lys His Gly Met Leu Val Arg Val Ala Gly Asp Gly Ile
450                 455                 460

Leu Met Ser Pro Pro Leu Ile Ile Ser Pro Glu Glu Ile Asp Glu Leu
```

```
465                 470              475             480
Ile Ser Ile Tyr Gly Lys Ala Leu Lys Ala Thr Glu Glu Lys Val Lys
                485              490              495
Glu Leu Lys Ala Gln His Lys Lys
            500
```

REGULATION OF PLANT FERTILITY BY MODULATION OF GABA LEVELS IN FLOWERS

This application claims the priority of U.S. Provisional Application Ser. No. 60/300,513, filed Jun. 22, 2001, the entire disclosure of which is specifically incorporated herein by reference. The government may own rights in this application pursuant to grant number DE-FG02-96ER20240 from the U.S. Department of Energy.

BACKGROUND OF THE INVENTION

I. Field of the Invention

The present invention relates generally to the field of plant molecular and cellular biology. More particularly, it concerns methods and compositions comprising altering fertility in plants through modulation of flower GABA levels.

II. Description of Related Art

The goal of plant breeding is to combine various desirable traits in a single variety/hybrid. Breeding techniques take advantage of a plant's method of pollination. There are two general methods of pollination: a plant self-pollinates if pollen from one flower is transferred to the same or another flower of the same plant. A plant cross-pollinates if pollen comes to it from a flower on a different plant. Control of the mode of fertilization is crucial to a successful plant breeding scheme.

One use of plant breeding techniques is the development of hybrid varieties. This is because a number of important crop plants exhibit hybrid vigor, whereby hybrid plants are grown by farmers because they exhibit enhanced agronomic characteristics, including more vigorous growth. As the hybrid crops are preferred, development of hybrid varieties of seed is important to the seed industry.

For production of hybrid crops, it is generally necessary to take steps to prevent self-pollination. In the case of hybrid maize production, this is typically achieved by physically removing the male reproductive flower portions, or tassels, prior to pollen shed. Although effective, the technique is highly labor intensive. Further, in plant species with individual flowers with both male and female reproductive organs, this can be difficult or impossible and another system for regulating fertility is generally needed.

Another means for controlling self pollination is the use of genetic male or self-sterility. A number of genes conferring male sterility have been described, for example, in U.S. Pat. No. 3,861,709, U.S. Pat. No. 3,710,511, U.S. Pat. No. 4,654,465, and U.S. Pat. No. 5,625,132. However, these genetic factors, whether nuclear or cytoplasmic, can be difficult to stably maintain in parent lines. Where cytoplasmic male sterility (CMS) is used, hybrid seed production requires three inbred lines: (1) a cytoplasmically male-sterile line having a CMS cytoplasm; (2) a fertile inbred with normal cytoplasm, which is isogenic with the CMS line for nuclear genes ("maintainer line"); and (3) a distinct, fertile inbred with normal cytoplasm, carrying a fertility restoring gene ("restorer" line). The CMS line is propagated by pollination with the maintainer line, with all of the progeny being male sterile, as the CMS cytoplasm is derived from the female parent. Therefore, although possible, maintenance of the male sterile line can be difficult and labor intensive. Further, the male sterility trait may introduce undesirable characteristics in the plant. For example, some cytoplasmic male sterility factors have been associated with increased susceptibility to fungal pathogens.

Various chemical gametocides have also been described for control of pollination. Gametocides affect processes or cells involved in the development, maturation or release of pollen. Plants treated with such gametocides are rendered male sterile, but typically remain female fertile. The use of chemical gametocides is described, for example, in U.S. Pat. No. 4,936,904. While use of gametocides has proved beneficial in some cases, they have yet to be adopted for widespread use.

Although the prior art has provided useful systems for the regulation of plant fertility, there is still a great need in the art for improved systems for regulating plant fertility. In particular, there is a need for a system of inducing self-sterility that avoids the requirement for costly emasculation of plants or complicated breeding schemes. The development of such a new system would improve plant breeding techniques and represent an important advance in the field of agriculture.

SUMMARY OF THE INVENTION

In one aspect, the invention provides a method of modulating the fertility of a plant comprising treating said plant with GABA or a GABA analog, including known or candidate modulators of GABA metabolism or GABA levels. In the method, any GABA analog could be used, for example, a GABA analog selected from the group consisting of forskolin, gabapentin and pregabalin, 4-cis aminocrotonic acid, 3-hydroxy-4-methylamino-4,5,6,7-tetrahydro-1,2-benzisoxazole (N-methyl-exo-THPO), Tetrahydroisoxazolo pyridin-3-ol (THIP), Imidazole-4-acetic acid, Isoguvacine, Muscimol, Baclofen, Cis-aminocrotonic acid (CACA) and Trans-aminocrotonic acid (TACA). The plant can be a monoecious plant or dioecious plant. The plant can also be a dicotyledonous plant, for example, an *Arabidopsis thaliana*, tobacco, tomato, potato, sugar beet, pea, carrot, cauliflower, broccoli, soybean, canola, sunflower, alfalfa, or cotton plant. The plant may also be a monocotyledonous plant, for example, a wheat, maize, rye, rice, turfgrass, oat, barley, sorghum, millet, or sugarcane plant.

The method may be further defined, in certain embodiments of the invention, as a method of creating a male sterile plant, wherein treating said plant comprises treating the male portion of flowers on said plant. The modulating may comprise rendering said plant sterile, including self-sterile. Treating may comprise treating any plant part, such as one or more flowers, and may comprise treating the whole plant, for example, by an over the top application of the GABA or GABA analog.

In another aspect, the invention provides a method of modulating the fertility of a plant comprising treating said plant with a GABA transaminase inhibitor. Any suitable GABA transaminase inhibitor could be used. In certain embodiments of the invention, the inhibitor is selected from the group consisting of (S)-4-Amino-5-fluoropentanoic Acid, 4-Amino-2-(substituted methyl)-2-butenoic Acids, 4-Amino-5-fluoropent-2-enoic Acid, gamma-vinyl GABA [D,L-4-amino-hex-5-enoic acid (Vigabatrin(R))] and Valproate. The plant can be a monoecious plant or dioecious plant. The plant can also be a dicotyledonous plant, for example, an *Arabidopsis thaliana*, tobacco, tomato, potato, sugar beet, pea, carrot, cauliflower, broccoli, soybean, canola, sunflower, alfalfa, or cotton plant. The plant may also be a monocotyledonous plant, for example, a wheat, maize, rye, rice, turfgrass, oat, barley, sorghum, millet, or sugarcane plant.

The method may be further defined, in certain embodiments of the invention, as a method of creating a male sterile plant, wherein treating said plant comprises treating the male portion of flowers on said plant. The modulating may comprise rendering said plant sterile, including self-sterile. Treating may comprise treating any plant part, such as one or more flowers, and may comprise treating the whole plant, for example, by an over the top application of the GABA transaminase inhibitor to a flower.

In yet another aspect, the invention provides a method of restoring the fertility of a plant having flowers rendered self-sterile by elevated GABA levels comprising treating said plant with a GABA inhibitor. Potentially any GABA inhibitor could be used with the invention, for example, guvacine, (R)-nipecotic acid, Tiagabine, anticonvulsant 1-(2-(((diphenylmethylene)amino)oxy)ethyl)-1,2,5, 6-tetrahydro pyridinecarboxylic acid hydrochloride (NNC-711, Bicuculline, Pitrazepin, Benzyl penicillin, securinine, Phaclofen, CGP35348, Picrotoxin, 1,2,5,6-tetrahydopyridine-4-yl, and methylphophinic acid. The plant used may be further defined as comprising a mutated POP2 gene. The plant may also comprise transgenic antisense POP2 gene, including a plant having decreased POP2 expression as a result of RNA interference (RNAi) The plant may be of any species, such as a dicotyledonous plant, including an *Arabidopsis thaliana*, tobacco, tomato, potato, sugar beet, pea, carrot, cauliflower, broccoli, soybean, canola, sunflower, alfalfa, or cotton plant. The plant may also be a monocotyledonous plant, including a wheat, maize, rye, rice, turfgrass, oat, barley, sorghum, millet, or sugarcane plant. Treating may comprise treating any plant part, such as one or more flowers, and may comprise treating the whole plant, for example, by an over the top application of the GABA inhibitor to a flower.

In still yet another aspect of the invention, a method of plant breeding is provided comprising a) obtaining first and second plants; b) treating said first plant with GABA or a GABA analog; and c) pollinating the first plant with pollen from said second plant. The pollination can be carried out by any means, including allowing natural pollination to occur or by manual pollination. The first plant may, in certain embodiments of the invention, be rendered self-sterile following said treating. Examples of GABA analogs that could be used include forskolin, gabapentin and pregabalin, 4-cis-aminocrotonic acid, 3-hydroxy-4-methylamino-4,5,6,7-tetrahydro-1,2-benzisoxazole (N-methyl-exo-THPO), Tetrahydroisoxazolo pyridin-3-ol (THIP), Imidazole-4-acetic acid, Isoguvacine, Muscimol, Baclofen, Cis-aminocrotonic acid (CACA) and Trans-aminocrotonic acid (TACA). The plants may be of any species, such as a dicotyledonous plant species, including an *Arabidopsis thaliana*, tobacco, tomato, potato, sugar beet, pea, carrot, cauliflower, broccoli, soybean, canola, sunflower, alfalfa, or cotton plant. The plants may also be from a monocotyledonous plant species, including a wheat, maize, rye, rice, turfgrass, oat, barley, sorghum, millet, or sugarcane plant. Treating may comprise treating any plant part, such as one or more flowers, and may comprise treating the whole plant, for example, by an over the top application of the GABA or GABA analog to a flower.

In still yet another aspect, the invention provides a method of plant breeding comprising a) obtaining first and second plants; b) treating said first plant with a GABA transaminase inhibitor; and c) pollinating the first plant with pollen from said second plant. The pollination can be carried out by any means, including allowing natural pollination to occur or by manual pollination. The first plant may, in certain embodiments of the invention, be rendered self-sterile following said treating. Examples of GABA transaminase inhibitor that could be used include (S)-4-Amino-5-fluoropentanoic Acid, 4-Amino-2-(substituted methyl)-2-butenoic Acids, 4-Amino-5-fluoropent-2-enoic Acid, gamma-vinyl GABA [D,L-4-amino-hex-5-enoic acid (Vigabatrin(R))] and Valproate. The plants may be of any species, such as a dicotyledonous plant species, including an *Arabidopsis thaliana*, tobacco, tomato, potato, sugar beet, pea, carrot, cauliflower, broccoli, soybean, canola, sunflower, alfalfa, or cotton plant. The plants may also be from a monocotyledonous plant species, including a wheat, maize, rye, rice, turfgrass, oat, barley, sorghum, millet, or sugarcane plant. Treating may comprise treating any plant part, such as one or more flowers, and may comprise treating the whole plant, for example, by an over the top application of the GABA transaminase inhibitor.

In still yet another aspect, the invention provides a method of screening for a candidate GABA analog comprising the steps of: a) obtaining a test plant; b) treating said test plant with a candidate GABA analog; and c) detecting the effect of said candidate GABA analog on the fertility of the test plant. In certain embodiments of the invention, detecting comprises detecting a decrease in the fertility of the plant. The plant may or may not be a monoecious or dioecious plant. The plant may be of any species, such as a dicotyledonous plant, including an *Arabidopsis thaliana*, tobacco, tomato, potato, sugar beet, pea, carrot, cauliflower, broccoli, soybean, canola, sunflower, alfalfa, or cotton plant. The plant may also be a monocotyledonous plant, including a wheat, maize, rye, rice, turfgrass, oat, barley, sorghum, millet, or sugarcane plant. Treating may comprise treating any plant part, such as one or more flowers, and may comprise treating the whole plant, for example, by an over the top application of the GABA analog to a flower on the test plant.

In still yet another aspect, the invention provides a method of screening for a candidate GABA transaminase inhibitor comprising the steps of: a) obtaining a test plant; b) treating said test plant with a candidate GABA transaminase inhibitor; and c) detecting the effect of said candidate GABA transaminase inhibitor on the fertility of the test plant. In certain embodiments of the invention, detecting comprises detecting a decrease in the fertility of the plant. The plant may or may not be a monoecious or dioecious plant. The plant may be of any species, such as a dicotyledonous plant, including an *Arabidopsis thaliana*, tobacco, tomato, potato, sugar beet, pea, carrot, cauliflower, broccoli, soybean, canola, sunflower, alfalfa, or cotton plant. The plant may also be a monocotyledonous plant, including a wheat, maize, rye, rice, turfgrass, oat, barley, sorghum, millet, or sugarcane plant. Treating may comprise treating any plant part, such as one or more flowers, and may comprise treating the whole plant, for example, by an over the top application of the GABA analog to a flower on the test plant.

In still yet another aspect, the invention provides a method of screening for a candidate GABA inhibitor comprising the steps of: a) obtaining a test plant exhibiting decreased fertility as a result of elevated GABA levels; b) treating said test plant with a candidate GABA inhibitor; and c) detecting the effect of said candidate GABA inhibitor on the fertility of the test plant. In one embodiment of the invention, the test plant comprises a mutation in the POP2 gene. In another embodiment, the test plant comprises a transgenic POP2 gene, and may also have reduced POP2 levels by antisense or RNAi technologies. The detecting may, in certain embodiments of the invention, comprise detecting a restoration of fertility following the treating.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 2A–2B) Final stages of pollen tube growth on wild type ovules, diagrammed (solid tube, FIG. 2A) or as observed with scanning electron microscopy (FIG. 2B, as presented previously in Wilhelmi and Preuss, 1996); tubes emerge from the septum (s), navigate up the funiculs (f), and enter the micropyle (m). (FIG. 2C) Scanning electron micrograph of aberrant pollen tube growth on pop2-1 ovules (Wilhelmi and Preuss, 1996). (FIG. 2D–2K) Sections of ovules from wild type (FIG. 2E, 2F, 2I, 2J) and pop2-1 ovules (FIG. 2G, 2K); transverse and cross sections were prepared as diagrammed in D and H, respectively. Anti-GABA localization was detected with silver (FIG. 2E, 2I) or TRITC (FIG. 2F–2G, 2J–2K). Large quantities of GABA were detected in a subset of the inner integument cells (arrow) that surrounds the micropyle (arrowhead); elevated GABA was apparent throughout the pop2-1 ovules (FIG. 2G, 2K).

(FIG. 4A) Phylogenetic relationship of class III transaminases, determined by Megalign analysis software (DNAStar, Madison, Wis.). Genbank accession numbers are indicated for each protein, and the amino acid substrate is shown in parentheses. POP2 is a single copy Arabidopsis gene and is closely related to genes with unknown functions that are present in rice, Capsicum (pepper) and tomato. (FIG. 4B) The protein sequence adjacent to the conserved pyridoxal phosphate cofactor binding site (*) of GABA transaminases was aligned using ClustalW (http://www.ebi-.ac.uk/clustalw) and boxshading software (http://www.ch.embnet.org/software/BOX_form.html). Dashes indicate gaps introduced to maximize alignment; residues identical or similar in a majority of sequences are shaded (black and gray, respectively). The POP2 protein is a class III transaminase (BLAST $P<1\times10^{-11}$) with a predicted, highly conserved binding site for a pyridoxal phosphate cofactor.

FIGS. 6A and B: (FIG. 6A) GABA levels in flowers from primary and secondary inflorescences. As can be seen, it was found that while GABA levels remained the same in flowers of primary and secondary inflorescence of wild type plants, there was a significant difference in pop2-1 flowers between the primary and secondary inflorescences (FIG. 6B) Seed count in siliques of primary and secondary inflorescences. In pop2-1, siliques in the secondary branches have more seeds than those in the primary branch.

FIGS. 7A and B: (FIG. 7A) Accumulation of GABA in pop2-1 mutant. Flowers isolated from two additional POP2 mutant lines (pop2-2 and pop2-3) also exhibited an increase in GABA levels relative to the wild type flowers. Interestingly, the increase in these two lines was less than in pop2-1 flowers. (FIG. 7B) Control to demonstrate that samples were equally loaded. Duplicate dot blots were probed with antibodies raised against glutamate and did not show variation similar to that for GABA among the mutant lines.

FIGS. 8A and B: (FIG. 8A) Dot blot containing total amino acids isolated from leaves, pollen and ovules of wild type and pop2-1 plants probed with antibodies raised against GABA. The GABA levels inpop2-1 leaves were lower than that found inpop2-1 ovules or pollen, although they were higher than the levels in wild type leaves. The GABA levels were higher in pop2-1 pollen and ovules compared to the corresponding wild type organs. The increased accumulation observed in male (pollen) and female (ovule) tissues is consistent with the self-sterile phenotype of pop2-1 flowers. (FIG. 8B) Control dot blot containing total amino acids isolated from leaves, pollen and ovules of wild type and pop2-1 plants probed with antibodies raised against glutamate.

DETAILED DESCRIPTION OF THE INVENTION

The current invention overcomes deficiencies in the prior art by providing methods for the manipulation of fertility in plants. Also provided by the invention are assays for the identification of compounds having such an effect on plant fertility. The assays provide an alternative to animal testing models. The methods of the invention relate to the finding that GABA accumulation in reproductive tissues can cause self-sterility in plants. In particular, the studies by the inventors elucidated the role of GABA accumulation in the self-sterility phenotype exhibited by the *A. thaliana* pop2 mutation. Therefore, by manipulating GABA accumulation in plant reproductive tissues in accordance with the invention, plant fertility can be altered. In this way, self-fertilization can be prevented. The technique represents a significant advance, potentially eliminating the need for labor intensive manual techniques for prevention of self-fertilization or the use of nuclear or cytoplasmic genetic male sterility factors that may be difficult to propagate and can be associated with various deleterious traits. In accordance with the invention, self-sterility can be induced by artificially increasing GABA levels in the reproductive tissues, for example, by administering GABA, a GABA analog or a GABA transaminase inhibitor.

I. Elucidation of the Role of GABA in Plant Fertility

Previous studies showed that specific defects in pollen tube guidance constitute the basis for self-sterility in an *Arabidopsis* mutant that exhibits a 300 fold reduction in seed production compared to wild type (Wilhelmi and Preuss, 1996). It was also previously shown that pollen tube guidance was the only apparent defect in this mutant plant; the pollen tube did not adhere to pistil cells (funiculus of the ovule) and grew in random directions throughout the ovary instead of growing towards the normal target, the micropyle of the ovule (Wilhelmi and Preuss, 1996; see also FIG. 1A and 1B; and FIG. 2B, C). In addition, it was determined that this mutant is self-sterile; the guidance defect only arises when male and female tissues carry the mutation. At that time, two genetic loci, designated pop2-1 and pop3-1, were believed necessary for sterility (Wilhelmi and Preuss, 1996). However, subsequent studies carried out by the inventors have indicated that the pop2-1 locus alone is sufficient to render the plant sterile and that a closely segregating embryo lethal mutation resulted in the erroneous prior implication of the pop3-1 locus in sterility.

A. Identification of POP2 as an Omega Aminotransferases

Figure 3:
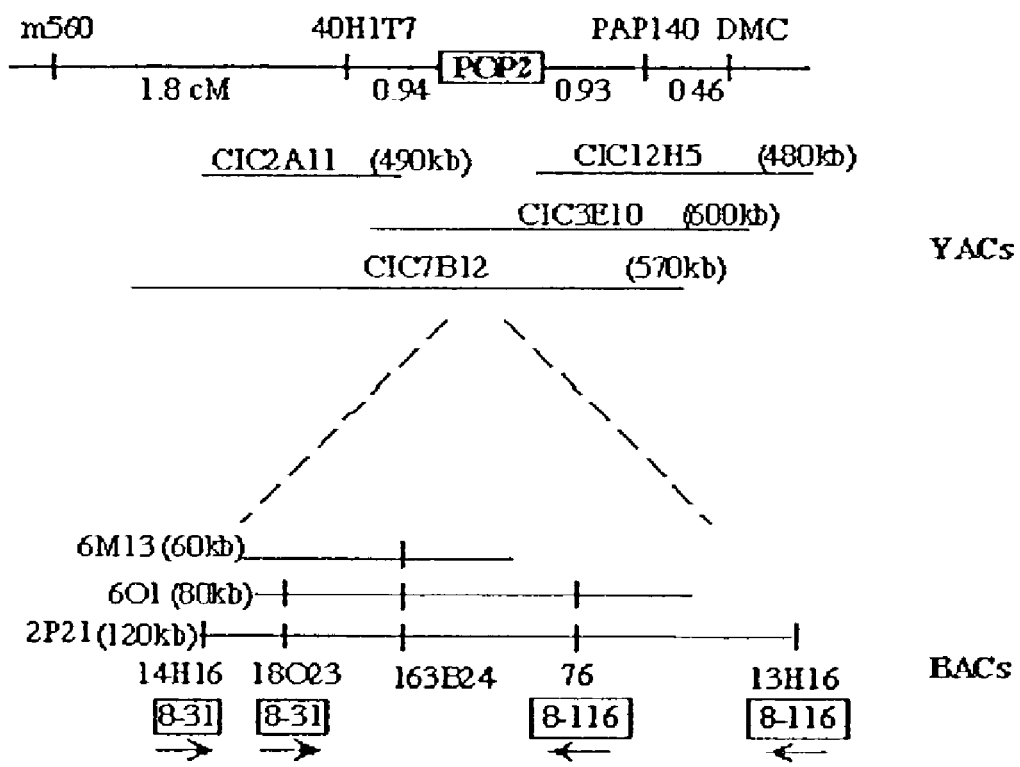
FIG. 3: Mapping of pop2-1 to chromosome 3. DNA polymorphisms were used to define the genetic map position of the POP2 gene to chromosome 3 of *Arabidopsis*. Additional genetic markers were identified as needed, and these were used to locate the gene on a small interval on the DNA sequence map.
Figure 4:
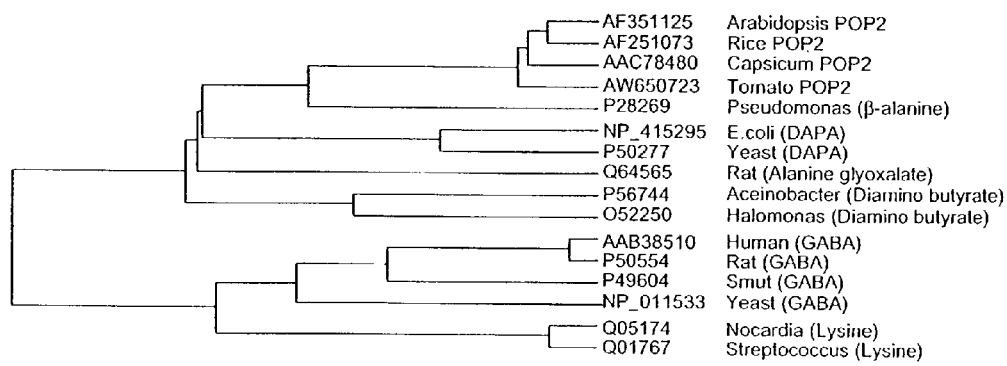
FIG. 4A–4B: Phylogenetic tree for POP2 protein sequence.

The pop2-1 mutation and its map location were previously used to clone the POP2 gene through a map-based approach (Laura Wilhelmi, Ph.D. thesis, University of Chicago and FIG. 3). Upon transformation into pop2-1 mutant lines, the cloned gene was able to restore fertility. Based on protein homology searches, at that time it was suggested that POP2 might encode an aminotransferase, with highest homology to DAPA (Diamino Pelargonic acid) aminotransferases involved in biotin biosynthesis (Laura Wilhelmi, Ph.D. thesis, University of Chicago and FIG. 3). However, subsequent protein sequence analysis involving updated genome sequence databases carried out by the inventors revealed that the POP2 protein sequence has an even greater homology to omega aminotransferases (FIG. 4). These enzymes are involved in the biosynthesis and catabolism of omega amino acids such as β-alanine, ornithine and GABA (Gamma amino butyric acid).

B. Accumulation of GABA in pop2 Sterile Flowers

Figure 5:
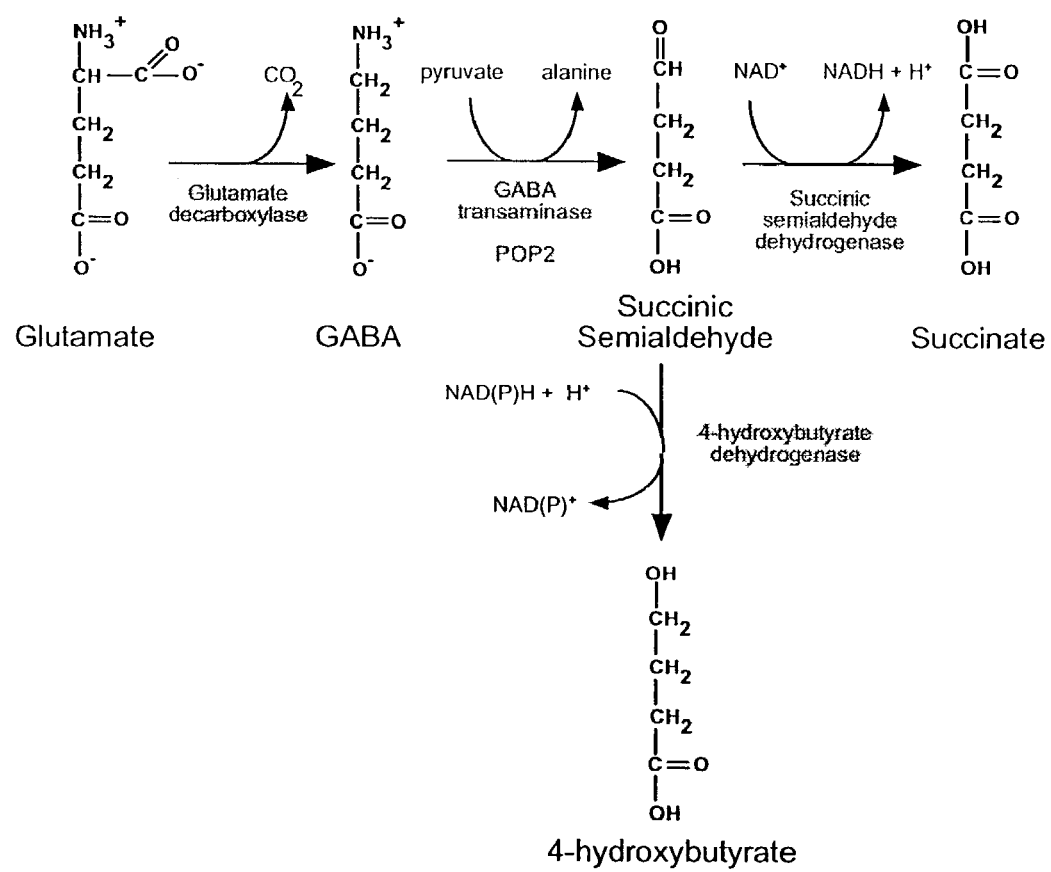
FIG. 5: Biochemical pathways involving the GABA shunt (Shelp et al., 1999). In the pathway, glutamate is converted to GABA which is then broken down to succinic semialdehyde by GABA transaminase. Succinic semialdehyde is then converted to succinate before it enters the KREB's cycle or to 4-hydroxybutyrate.

To determine which omega amino acids could be a substrate of POP2, the concentration of individual free amino acids in wild type and mutant flowers was determined. The results of the analysis are given in Table 1. As can be seen, GABA levels were found to be ~100 times higher in pop2-1 flowers compared to wild type flowers. The concentration of β-alanine was also slightly higher in pop2-1 flowers relative to the wild type flowers (~5 fold). The experiment was repeated twice (three times total), yielding an average and standard deviation (Table 1). Within the margin of error, no other amino acids showed variation more than two fold between the wild type and pop2-1 flowers. Genetic analysis indicated that the pop2-1 mutation causes a loss of function of the POP2 gene. Therefore, the significant increase of GABA levels in pop2-1 flowers suggests that the normal function of POP2 is in GABA catabolism. Biochemical pathways involving GABA, called the GABA shunt were previously elucidated in other organisms (see, e.g., Shelp et al., 1999; FIG. 5). In this pathway, glutamate is converted to GABA, which is then broken down to succinic semialdehyde by GABA transaminase. Succinic semialdehyde is then converted to succinate before it enters the KREB's cycle or to 4-hydroxybutyrate. Based on sequence homology to a transaminase and the accumulation of GABA in the pop2-1 mutant (FIG. 7 and Table1), it was concluded that POP2 encodes a GABA transaminase in Arabidopsis.

The significant increase in GABA levels in pop2-1 flowers indicates that wild-type POP2 most likely functions by removing an amino group from GABA. Biochemical assays indicate that GABA transaminases move an amino group to either pyruvate or α-keto glutarate. Both activities exist in many species, including plants (Shelp et al, 1999), although only the α-keto glutarate class has been characterized sufficiently to warrant inclusion in phylogenetic analyses. The significant homology between POP2 and a β-alanine pyruvate transaminase suggests that POP2 likely uses pyruvate as an amino acceptor.

TABLE 1

Concentration of free amino acids in wild type and pop2 mutant flowers

| Amino acid | Wild type (µmol/g) | pop2 flowers (µmol/g) | Fold difference |
|---|---|---|---|
| GABA | 0.20 ± 0.06 | 20.62 ± 3.50 | 104.51 |
| β-alanine | 0.16 ± 0.05 | 0.81 ± 0.19 | 5.17 |
| Alanine | 1.42 ± 0.49 | 1.48 ± 0.64 | 1.04 |
| Arginine | 0.39 ± 0.06 | 0.35 ± 0.05 | 0.89 |
| Asparagine | 1.60 ± 0.82 | 2.01 ± 1.61 | 1.25 |
| Aspartic acid | 2.38 ± 0.71 | 1.44 ± 0.25 | 0.60 |
| Ethanolamine | 0.59 ± 0.59 | 0.54 ± 0.30 | 0.91 |
| Glycine | 2.13 ± 0.49 | 3.65 ± 0.74 | 1.71 |
| Glutamic acid | 3.45 ± 0.79 | 2.58 ± 0.46 | 0.75 |
| Glutamine | 2.51 ± 1.23 | 5.50 ± 5.24 | 2.19 |
| Histidine | 0.39 ± 0.07 | 0.24 ± 0.03 | 0.61 |
| Isoleucine | 0.20 ± 0.19 | 0.23 ± 0.02 | 1.18 |
| Leucine | 0.38 ± 0.05 | 0.32 ± 0.01 | 0.83 |
| Lysine | 0.24 ± 0.05 | 0.24 ± 0.03 | 1.01 |
| 1-Methyl Histidine | 0.09 ± 0.01 | 0.12 ± 0.03 | 1.24 |
| Ornithine | 0.20 ± 0.10 | 0.12 ± 0.04 | 0.61 |
| Phenylalanine | 0.10 ± 0.03 | 0.06 ± 0.05 | 0.59 |
| Phosphoserine | 0.11 ± 0.03 | 0.09 ± 0.01 | 0.84 |
| Proline | 4.93 ± 1.13 | 2.66 ± 0.74 | 0.54 |
| Serine | 2.47 ± 0.89 | 2.16 ± 0.50 | 0.87 |
| Threonine | 1.65 ± 0.44 | 1.40 ± 0.29 | 0.85 |
| Tyrosine | 0.23 ± 0.30 | 0.06 ± 0.05 | 0.26 |
| Tryptophan | 0.33 ± 0.09 | 0.08 ± 0.14 | 0.23 |
| Valine | 0.66 ± 0.08 | 0.68 ± 0.09 | 1.02 |

Gas chromotagraphy coupled with Mass spectrometry analysis of total flower extracts from wild-type and pop2-1 mutants revealed that succinate levels remain unaltered (Table 2). Similarly, 4-hydroxy butanoate levels were also unaltered in the wild type and mutant flower extracts (Table 2). In addition, it is known that succinic semialdehyde is produced as an intermediate in the tyrosine and vitamin B6 metabolism pathways besides the GABA shunt pathway (www.genome.adjp/dbget-bin/www_bget?cpd:C00232). Taken together, these results indicate that sterility in pop2 plants is a consequence of increases in GABA levels rather than downstream deficiencies.

TABLE 2

Concentrations of the compounds involved in the GABA shunt pathway.

| GABA shunt components | POP2 (µmol g$^{-1}$) | pop2-1 (µmol g$^{-1}$) | Fold difference |
|---|---|---|---|
| glutamate | 3.45 ± 0.73 | 2.55 ± 0.60 | 0.74 |
| GABA | 0.20 ± 0.06 | 22.27 ± 0.45 | 113.00 |

TABLE 2-continued

Concentrations of the compounds involved in the GABA shunt pathway.

| GABA shunt components | POP2 ($\mu$mol g$^{-1}$) | pop2-1 ($\mu$mol g$^{-1}$) | Fold difference |
|---|---|---|---|
| Succinic semialdehyde | <0.01 | <0.01 | ND* |
| Succinic acid | 3.45 ± 0.73 | 2.55 ± 0.60 | 0.74 |
| 4-hydroxybutyrate | .096 ± 0.04 | 0.18 ± 0.03 | 1.875 |

*ND = Not determined

C. Increased GABA Levels Correlate with Decreased Fertility

Wild type Arabidopsis plants exhibit limited branching in their inflorescence stems. In contrast, pop2-1 sterile plants have extensive branching, typical of many sterile plants. In pop2-1, siliques (fruits) in the secondary branches have more seeds than those in the primary branch (FIG. 6B). To investigate whether this difference in fertility also correlated with GABA levels in the flowers of the primary and secondary branches, total amino acids were quantified from flowers isolated separately from these two types of branches. As shown in FIG. 6A, it was found that GABA levels remained the same in primary and secondary branch flowers of wild type plants. In pop2-1, a significant decrease in GABA levels was found in secondary branch flowers, which showed increased fertility compared to primary branch flowers. The concentration of all other amino acids remained the same in pop2-1 primary and secondary branch flowers. These results indicated that increased GABA levels correlate with decreased fertility.

Figure 9:
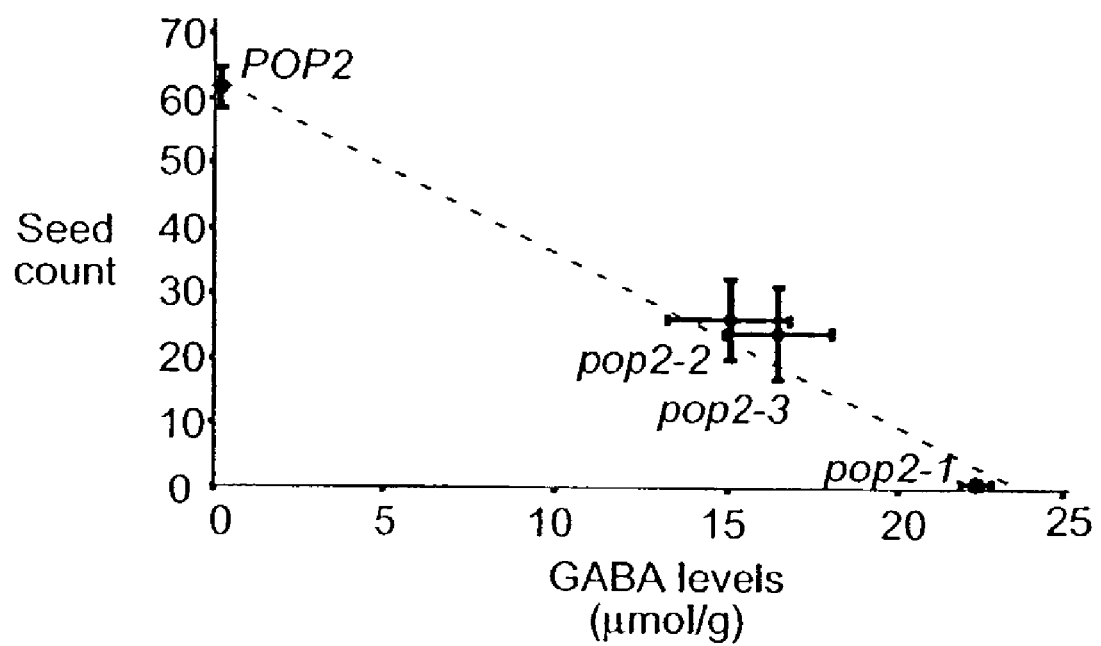
FIG. 9: GABA levels in POP2 tissues Correlation between floral GABA concentration and seed production (correlation coefficient, R2=0.98). Data represent the mean obtained from triplicate determinations (± standard error), each with a sample size of 5 flowers (GABA) or 6 fruits (seed yield) Comparison of the levels of floral GABA and fertility in three pop2 mutants revealed an inverse correlation, suggesting pollen tube growth becomes more random with increasing GABA.

To confirm the relationship between GABA levels and fertility, additional plants were isolated with mutations in the POP2 gene. Two additional mutant lines were identified with insertions of transfer DNA (T-DNA) into the pop2 gene (Krysan et al., 1999). Comparison of floral GABA levels and fertility in these two alleles along with those in pop2-1 revealed an inverse correlation, suggesting pollen tube growth becomes more random with increasing GABA levels (FIG. 9). These results are similar to the GABA concentration dependent migration pattern of neuroblasts: GABA directs proper migration at $\mu$M concentrations, but stimulates random motility at $\mu$M levels (Barker et al, 1998). GABA is a neurotransmitter that triggers action potentials in the mammalian nervous system and also serves as a chemotrophic factor that promotes the out-growth of cerebellar cells. The elucidation of the function of POP2 provides evidence that GABA promotes polarized cell guidance in both the plant and animal kingdoms. The discovery offers an opportunity to characterize the role of GABA receptors and downstream signaling molecules in pollen tube guidance. Furthermore, the results indicate the potential to use pollen tube growth as a model for the chemotrophic role of GABA in the mammalian nervous system. For example, GABA agonists and antagonists could be tested in plants prior to or in lieu of performing animal studies.

D Localization of GABA

To further understand the functional significance of GABA accumulation, further studies were carried out to identify the organs of pop2-1 plants in which GABA levels were significantly increased relative to wild type. Total amino acids were isolated from leaves, pollen and ovules of wild type and pop2-1 plants. Dot blots containing these extracts were probed with antibodies raised against GABA or glutamate. As shown in FIG. 8, the GABA levels in pop2-1 leaves was lower than that found in pop2-1 ovules or pollen, although it was higher than the levels in wild type leaves. The GABA levels were higher in pop2-1 pollen and ovules compared to the corresponding wild type organs. The increased accumulation observed in male (pollen) and female (ovule) tissues is consistent with the self-sterile phenotype of pop2-1 flowers. As wild-type pollen tubes successfully fertilize the ovules in a pop2 pistil, and pop2 mutant pollen tubes are fertile in a wild-type pistil, sterility may involve an interaction between male and female tissues. Therefore, for induction of sterility with GABA, it may be desired to first serially determine a threshold level for a given target species.

Figure 10:
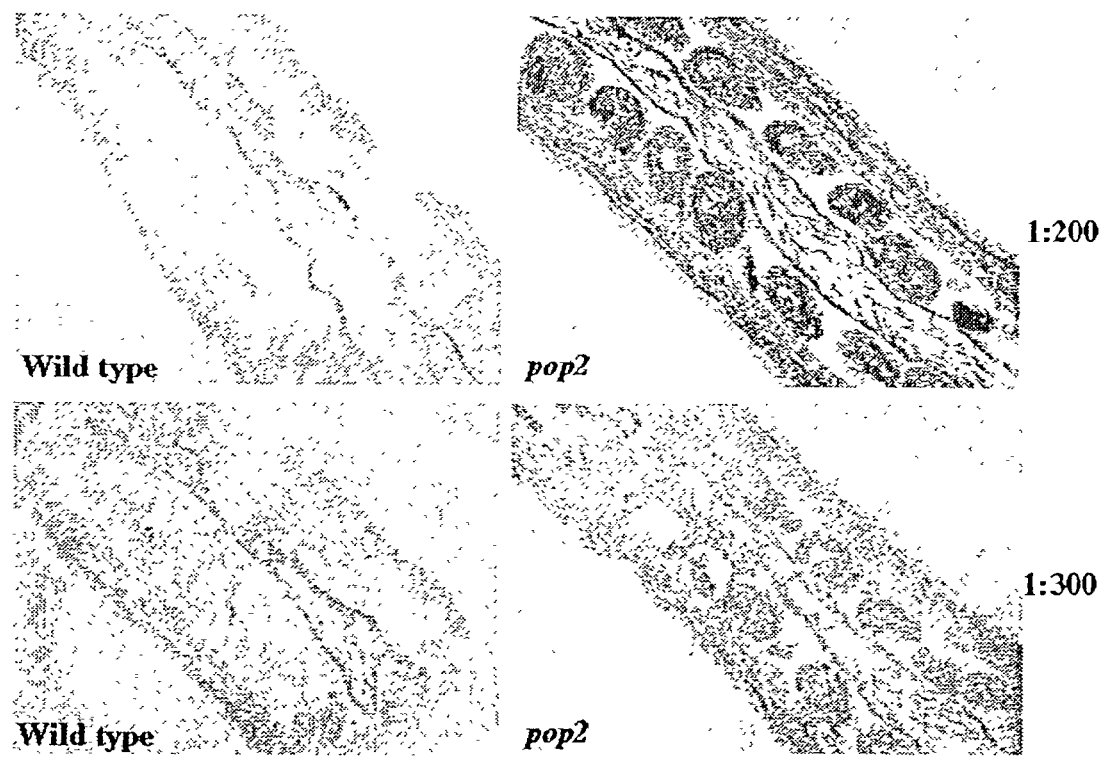
FIG. 10: Cell-specific localization of GABA performed within pistils. Thin sections of pollinated wild type or pop2-1 pistils were made and probed with anti-GABA antibodies. Consistent with the GABA quantification and dot blot results, pop2-1 pistils showed increased accumulation of GABA relative to the wild type pistils.

To obtain clues about the role of GABA in pollen tube guidance, cell-specific localization of GABA was performed within pistils. Thin sections of pollinated wild type or pop2-1 pistils were made and probed with anti-GABA antibodies. Consistent with the GABA quantification and dot blot results described above, pop2-1 pistils showed increased accumulation of GABA relative to the wild type pistils (FIG. 10). The pistils used in these studies had been pollinated and therefore contained pollen tubes that had traveled through them and fertilized ovules. To investigate if there is any specific localization of GABA in the path that the pollen tube takes to the ovules, similar studies are being performed with unpollinated pistils.

The elevated GABA in pop2-1 ovules could result from increases in cells that normally accumulate GABA or from ectopic accumulation. To distinguish between these possibilities, GABA was immunolocalized in sections of wild type and mutant pistils, focusing on those areas where the pop2 mutant exhibited guidance defects (FIG. 1B, C). Ovules are attached to the septum surface by a funiculus (FIG. 1A). The inner and outer ovule integuments encase the embryo sac cells, including the egg; pollen tubes target the egg by growing along the septum, up the funiculus and entering the micropyle between the integuments, subsequently releasing the sperm (FIG. 1A). Relative to the septum and funiculus, wild type ovules had a focus of GABA accumulation in the inner integument cells nearest the micropyle (FIG. 1E, F, I, J (n=48, 56, 78, 123 respectively); this subset of integument cells has not previously been implicated in directing pollen tube guidance. In pop2-1, the GABA pattern was similar to wild type but highly elevated throughout the septum and funiculus and ovule (FIG. 1G, K; n=66, 87, respectively). pop2 pollen tubes exhibit random growth and defective adhesion to funiculus cells, inappropriate growth on integument surfaces, and migration past the micropyle (Wilhelmi and Preuss, 1996); all of these sites are marked by unusually high levels of GABA. These increases in GABA may attract pop2 pollen tubes to inappropriate locations, resulting in sterility.

II. Induction and Utilization of Sterility

In accordance with the invention, manipulation of GABA levels can be used to modify the fertility of plants. For example, the invention overcomes the deficiencies of prior techniques by providing an inducible system for the production of self-sterile plants. In particular, the invention allows manipulation of GABA levels in reproductive tissues to artificially induce a self-sterile phenotype in plants. Alternatively, the invention provides methods for the restoration of fertility in plants with elevated levels of GABA by artificially diminishing the effect of GABA on fertility, for instance, by application of a GABA inhibitor.

An important application for the invention is plant breeding. For example, elevation of GABA levels in plant flowers can be used to induce self-sterility in plants, thereby facilitating outcrossing of plants. The technique avoids the need for labor intensive emasculation of plants or the use of genetic sterility systems that are difficult to maintain or are associated without deleterious traits.

The ability to efficiently outcross plants is important to plant breeding procedures. Plants can be heterozygous or homozygous. If the same alleles are present at a locus, there is said to be homozygosity at that locus. If they are different, there is said to be heterozygosity. In a completely inbred plant, essentially all loci are homozygous, absent spontaneous mutations or strong selection for a heterozygous state. Because, in some plants, homozygous loci can be deleterious to the plant, leading to reduced vigor and/or poor growth, use of inbred plants directly by the farmer may be less preferred. For example, maize exhibits "hybrid vigor" and thus is grown by farmers as a hybrid. That is, in general, hybrid maize will demonstrate greater vigor than will inbreds. Production of hybrids will therefore be of great interest to the breeder and grower. Further, new varieties of crops are typically produced by first preparing a hybrid cross between starting lines. Therefore, careful control of pollination is essential to plant breeding. However, absent human intervention, many plants will self-pollinate, rendering the breeding process unpredictable.

For hybrid production, the male and female parents are typically different elite inbreds derived from different heterotic backgrounds. Plants of both parents are then cultivated and allowed to grow until the time of flowering. Cross-pollination then must take place for production of hybrids. However, as indicated above, many plants will naturally self-pollinate and human intervention is normally required for hybrid production. Commonly, this requires emasculation, e.g., removal of the male reproductive parts of the plant prior to the time of pollen shed, to prevent self-fertilization. However, emasculation is time and labor intensive. Alternatively, nuclear or cytoplasmic genetic male sterility factors can be used. However, introduction of these traits may take labor intensive backcrossing of the trait into elite germplasm, propagation of the sterility trait in parent lines may require complicated breeding schemes and the sterility traits may be associated with linked deleterious traits. In accordance with the invention, however, this step can be replaced by artificially increasing GABA levels in the reproductive tissues, for example, by administering a GABA, a GABA analog or a GABA transaminase inhibitor.

Following emasculation, hybridization and fertilization takes place. Plants can be crossed by either natural or mechanical techniques. Natural pollination occurs when pollen is transported by gravity, wind, pollinating insects or animals or other natural vectors from the male reproductive parts of a flower to the receptive portions of the flower. In monoecious crops, such as maize, the male and female flower parts are positioned at different locations on the same plant. In dioecious plants, there are separate male and female plants.

Artificially directed pollination can be effected by hand or other manual techniques. Treatment of plants to induce sterility can be carried out on individual plants or by an over-the-top treatment of an entire field of parental plants. Commonly there will be a plant used as the male parent (the pollen donor) and a plant used as the female parent (the pollen recipient). In this case, the female parent is typically rendered male-sterile-by the treating and the outcrossed progeny will be obtained from the female parent. An appropriate male parent will be fertile with respect to the male reproductive tissues (male fertile), but may or may not be female-sterile.

Following treatment to render the female plant male sterile, plants are allowed to grow and natural or manual cross-pollination occurs. As a result of the induced male-sterility of the female parent plant, all the pollen from the male parent plant is available for pollination because the pollen of the female parent has previously been sterilized. Of course, during this hybridization procedure, the parental varieties are preferably grown such that they are isolated from other plants to minimize or prevent any accidental contamination of pollen from foreign sources. These isolation techniques are well within the skill of those skilled in this art.

In one embodiment of the invention, seed produced is a first generation seed capable of being grown into an $F_1$ hybrid plant, wherein both the first and second parent plants are inbred plants. In another embodiment, one or both of the first and second parent plants can be hybrids. Where an inbred plant is crossed with another, different, inbred plant, seed capable of growing into a first generation ($F_1$) hybrid plant is produced. This $F_1$ seed, the $F_1$ hybrid plants grown therefrom, and seed of that $F_1$ hybrid plant are aspects of the present invention. The goal of a process of producing an $F_1$ hybrid is to manipulate the genetic complement of plants to generate new combinations of genes which interact to yield new or improved traits (phenotypic characteristics). A process of producing an $F_1$ hybrid typically begins with the production and crossing of one or more inbred plants. In a preferred embodiment, crossing comprises the steps of:

(a) planting seeds of a first and a second parent plant;
(b) cultivating or growing the seeds of the first and second parent plants;
(c) treating at least the first plant with a modulator of GABA metabolism in order to increase the level of GABA in at least one flower on the first plant; and
(d) cross-pollinating the treated flower with pollen from the second parent plant.

Both parental plants may be allowed to continue to grow until maturity or the male rows may be destroyed after flowering is complete. Therefore, in certain embodiments, the technique may include the next step of: (e) harvesting seeds resulting from the cross-pollinating. Only seeds from the female parental plants are generally harvested to obtain outcrossed seeds. The collected seed represents a valuable commercial product which can be sold to farmers, processed, or employed in further breeding programs.

III. Modulating GABA in Plants

In one embodiment of the invention, certain known or candidate modulators of GABA metabolism or GABA may be applied to a plant or plant part. In one embodiment of the invention, the plant part is a flower, including the male and/or female portions thereof. Any suitable method may be employed for the application. For example, modulators of GABA metabolism, including a GABA inhibitor, GABA analog and GABA transaminase inhibitor, as well as any combinations thereof, can be applied in an aqueous or powdered solution to a plant. Treatment can be by an over-the-top application of the modulator to a single plant or part thereof, a selected collection of plants, a row of plants, a population of plants or an entire field of plants. Treatment will generally only be made to those plants for which alteration of fertility is desired, or of those plants which are used in assays provided herein for identification of candidate modulators of GABA metabolism or GABA analogs. For example, candidate compounds capable of elevating effective GABA levels in plants can be identified through the induction of a self-sterility phenotype upon application of the candidate compound to a test plant. Such candidates may elevate GABA levels by inhibiting the catabolism of GABA or may do so by stimulating GABA synthesis. Alternatively, such compounds may be GABA analogs which cause the same physiological activity of self-sterility as GABA.

The techniques of the invention can be carried out in large scale. For example, an assay of candidate GABA metabolism modulators can be carried out by treating a population of selected test plants with the candidate compound followed by determining the effect of the treating on the ability of the plant to produce progeny following self-pollination. Although potentially any plant could be used for the assay, A. thaliana represents one particularly useful organism for this purpose due to its convenience of use, including small size and short growth time to maturity. Self-sterility in A. thaliana is readily identifiable by the notable absence of elongated seed pods (siliques). Further verification of sterility is performed by opening siliques and visually confirming the reduction or absence of seeds. For larger scale analyses, groups of plants can be harvested, seed pods opened by mechanical means, and seeds collected after separating out plant debris. The yield of seeds per gram of plant material is easily determined by weighing the seeds.

It will be understood by those of skill in the art that it may be desired to specifically formulate compositions containing GABA, GABA analogs or modulators of GABA metabolism for application to plants. Such compositions will be known to those of skill in the art. Specific types of ingredients one may wish to include in such formulations are described in, for example, U.S. Pat. No. 6,242,382, the disclosure of which is specifically incorporated herein by reference in its entirety. Some examples of types of ingredients for inclusion with GABA, a GABA analog or a modulator of GABA metabolism in accordance with the invention are listed below, although those of skill in the art will understand that this list is non-limiting and intended for exemplary purposes only.

One ingredient that may be desired for inclusion with a GABA modulator or analog to be applied to plants is a surfactant. Suitable as surfactants include the alkali metal, alkaline earth metal or ammonium salts of aromatic sulfonic acids, e.g., ligno-, phenol-, naphthalene- and dibutylnaphthalenesulfonic acid, and of fatty acids of arylsulfonates, of alkyl ethers, of lauryl ethers, of fatty alcohol sulfates and of fatty alcohol glycol ether sulfates, condensates of sulfonated naphthalene and its derivatives with formaldehyde, condensates of naphthalene or of the naphthalenesulfonic acids with phenol and formaldehyde, condensates of phenol or phenolsulfonic acid with formaldehyde, condensates of phenol with formaldehyde and sodium sulfite, polyoxyethylene octylphenyl ether, ethoxylated isooctyl-, octyl-or nonylphenol, tributylphenyl polyglycol ether, alkylaryl polyether alcohols, isotridecyl alcohol, ethoxylated castor oil, ethoxylated triarylphenols, salts of phosphated triarylphenolethoxylates, lauryl alcohol polyglycol ether acetate, sorbitol esters, lignin-sulfite waste liquors or methylcellulose, or mixtures of these. Common practice in the case of surfactant use is to include about 0.5 to 25% by weight, based on the total weight of the solid mixture.

GABA modulators or analogs may also be comprised in a solid mixture for application to plants. In such instances, it may be desired to include one or more carrier materials with the active compound. Examples of carriers include mineral earths such as silicas, silica gels, silicates, talc, kaolin, attaclay, limestone, chalk, loess, clay, dolomite, diatomaceous earth, calcium sulfate, magnesium sulfate, magnesium oxide, ground synthetic materials, fertilizers such as ammonium sulfate, ammonium phosphate, ammonium nitrate, thiourea and urea, products of vegetable origin such as cereal meals, tree bark meal, wood meal and nutshell meal, cellulose powders, attapulgites, montmorillonites, mica, vermiculites, synthetic silicas and synthetic calcium silicates, or mixtures of these.

For liquid solutions, water-soluble compounds or salts may be included, such as sodium sulfate, potassium sulfate, sodium chloride, potassium chloride, sodium acetate, ammonium hydrogen sulfate, ammonium chloride, ammonium acetate, ammonium formate, ammonium oxalate, ammonium carbonate, ammonium hydrogen carbonate, ammonium thiosulfate, ammonium hydrogen diphosphate, ammonium dihydrogen monophosphate, ammonium sodium hydrogen phosphate, ammonium thiocyanate, ammonium sulfamate or ammonium carbamate.

Other exemplary components include binders such as polyvinylpyrrolidone, polyvinyl alcohol, partially hydrolyzed polyvinyl acetate, carboxymethylcellulose, starch, vinylpyrrolidone/vinyl acetate copolymers and polyvinyl acetate, or mixtures of these; lubricants such as magnesium stearate, sodium stearate, talc or polyethylene glycol, or mixtures of these; antifoams such as silicone emulsions, long-chain alcohols, phosphoric esters, acetylene diols, fatty acids or organofluorine compounds, and complexing agents such as: salts of ethylenediaminetetraacetic acid (EDTA), salts of trinitrilotriacetic acid or salts of polyphosphoric acids, or mixtures of these.

Examples of known GABA inhibitors that could be used in accordance with the invention for application to plants include guvacine, (R)-nipecotic acid, Tiagabine, anticonvulsant 1-(2-(((diphenylmethylene)amino)oxy)ethyl)-1,2,5, 6-tetrahydro pyridinecarboxylic acid hydrochloride, NNC-711, Bicuculline, Pitrazepin, Benzyl penicillin, securinine, Phaclofen, CGP35348, Picrotoxin, 1,2,5,6-tetrahydopyridine-4-yl, and methylphophinic acid (see, e.g., Krogsgaard-Larsen et al., 2000; Iversen, 2000; and Gerasimov et al., 2000).

Examples of know GABA analogues that could be used with the invention include forskolin, gabapentin and pregabalin, 4-cis aminocrotonic acid, 3-hydroxy-4-methylamino-4,5,6,7-tetrahydro-1,2-benzisoxazole (N-methylexo-THPO), Tetrahydroisoxazolo pyridin-3-ol (THIP), Imidazole-4-acetic acid, Isoguvacine, Muscimol, Baclofen, Cis-aminocrotonic acid (CACA) and Trans-aminocrotonic acid (TACA). (see, e.g., Jefferson, 2001; Devlin, 2001; Schousboe, 2000; and Potschka et al., 2000).

Example of known GABA transaminase inhibitors that could be used with the invention include (S)-4-Amino-5-fluoropentanoic Acid, 4-Amino-2-(substituted methyl)-2-butenoic Acids, 4-Amino-5-fluoropent-2-enoic Acid, gamma-vinyl GABA [D,L-4-amino-hex-5-enoic acid] (Vigabatrin®) and Valproate (see, e.g., Silverman et al., 1983; Silverman, 1986; Silverman et al., 1986; Johannessen, 2000; and Gerasimov et al., 2000).

Potentially any amount of a modulator of GABA metabolism may be applied with the invention that does not result in plant necrosis. Such levels will be determined through serial applications of mixtures to members of a population of plants otherwise grown under similar environmental conditions. Effects on plant viability as a result of the applications can be ascertained through visual identification of necrotic sectors on vegetative plant tissues.

IV. Assays for Identifying Modulators of GABA Metabolism and GABA Analogues

One important aspect of the invention comprises new assays for identification of modulators of GABA metabolism and GABA analogues. For example, the invention provides assays that allow utilization of the finding that increased floral levels of GABA are associated with self-infertility for the identification of new GABA analogs or modulators of GABA metabolism. In accordance with the invention, large numbers of GABA analogs could be screened by serial applications to plant flowers followed by identification of the self-sterile phenotype in the case of an actual GABA analog. Similarly, candidate inhibitors of GABA transaminase could be screened in the same way as the inhibition of GABA transaminase would result in increased GABA levels. Alternatively, GABA inhibitors could be screened by treating a plant with pre-existing elevated GABA levels with a candidate GABA inhibitor followed by screening for restoration of self-fertility.

The new assays are important in that they provide an alternative to animal testing. The assays are also significant given the major role that GABA plays in natural biochemical processes. For example, GABA is the major inhibitory neurotransmitter in the human central nervous system (CNS) (for review see Enna, 1983; Schwartz, 1988). A reduction in GABA neurotransmission has been implicated in the etiology of a variety of neurological disorders, including epilepsy (Krogsgaard-Larsen et al., 1988; Rebak et al., 1979). Therefore, identification of novel modulators of GABA metabolism may provide new means for treating a variety of medical conditions.

V. Plants

The term "plant," as used herein, refers to any type of plant. The inventors have provided below an exemplary description of some plants that may be used with the invention. However, the list is provided for illustrative purposes only and is not limiting, as other types of plants will be known to those of skill in the art and could be used with the invention.

A common class of plants exploited in agriculture are vegetable crops, including artichokes, kohlrabi, arugula, leeks, asparagus, lettuce (e.g., head, leaf, romaine), bok choy, malanga, broccoli, melons (e.g., muskmelon, watermelon, crenshaw, honeydew, cantaloupe), brussels sprouts, cabbage, cardoni, carrots, napa, cauliflower, okra, onions, celery, parsley, chick peas, parsnips, chicory, Chinese cabbage, peppers, collards, potatoes, cucumber plants (marrows, cucumbers), pumpkins, cucurbits, radishes, dry bulb onions, rutabaga, eggplant, salsify, escarole, shallots, endive, garlic, spinach, green onions, squash, greens, beet (sugar beet and fodder beet), sweet potatoes, swiss-chard, horseradish, tomatoes, kale, turnips, and spices.

Other types of plants frequently finding commercial use include fruit and vine crops such as apples, apricots, cherries, nectarines, peaches, pears, plums, prunes, quince almonds, chestnuts, filberts, pecans, pistachios, walnuts, citrus, blueberries, boysenberries, cranberries, currants, loganberries, raspberries, strawberries, blackberries, grapes, avocados, bananas, kiwi, persimmons, pomegranate, pineapple, tropical fruits, pomes, melon, mango, papaya, and lychee.

Many of the most widely grown plants are field crop plants such as evening primrose, meadow foam, corn (field, sweet, popcorn), hops, jojoba, peanuts, rice, safflower, small grains (barley, oats, rye, wheat, etc.), sorghum, tobacco, kapok, leguminous plants (beans, lentils, peas, soybeans), oil plants (rape, mustard, poppy, olives, sunflowers, coconut, castor oil plants, cocoa beans, groundnuts), fiber plants (cotton, flax, hemp, jute), lauraceae (cinnamon, camphor), or plants such as coffee, sugarcane, tea, and natural rubber plants.

Another economically important group of plants are ornamental plants. Examples of commonly grown ornamental plants include alstroemeria (e.g., *Alstoemeria brasiliensis*), aster, azalea (e.g., *Rhododendron* sp.), begonias (e.g., *Begonia* sp.), bellflower, bouganvillea, cactus (e.g., *Cactaceae schlumbergera truncata*), camellia, carnation (e.g., *Dianthus caryophyllus*), chrysanthemums (e.g., *Chrysanthemum* sp.), clematis (e.g., *Clematis* sp.), cockscomb, columbine, cyclamen (e.g., *Cyclamen* sp.), daffodils (e.g., *Narcissus* sp.), false cypress, freesia (e.g., *Freesia refracta*), geraniums, gerberas, gladiolus (e.g., *Gladiolus* sp.), holly, hybiscus (e.g., *Hibiscus rosasanensis*), hydrangea (e.g., *Macrophylla hydrangea*), juniper, lilies (e.g., *Lilium* sp.), magnolia, miniroses, orchids (e.g., members of the family *Orchidaceae*), petunias (e.g., *Petunia hybrida*), poinsettia (e.g., *Euphorbia pulcherima*), primroses, rhododendron, roses (e.g., *Rosa* sp.), snapdragons (e.g., *Antirrhinum* sp.), shrubs, trees such as forest (broad-leaved trees and evergreens, such as conifers) and tulips (e.g., *Tulipa* sp.).

VI. Definitions

As used herein, the term "allele" refers to any of one or more alternative forms of a gene, all of which alleles relate to one trait or characteristic. In a diploid cell or organism, the two alleles of a given gene occupy corresponding loci on a pair of homologous chromosomes.

As used herein, the term "cross-pollination" refers to fertilization by the union of two gametes from different plants.

As used herein, the term "flower" refers to both the male and female reproductive organs of a plant. It will be understood to those of skill in the art that some plants have separate male and female flowers either on a single plant (e.g., a monoecious plant) or on separate plants (dioecious plant) and that the term "flower" as used herein encompasses both male and female flowers.

As used herein, the term "GABA analog" refers to any chemical or other substance that causes a reduction in self-fertility in a plant treated with the GABA analog. The substance may be chemically similar to GABA, having the same functional groups, or may be different in structure, but act on GABA targets within the plant to cause an increase in self-sterility. Another name often used to refer to such an analog is an "agonist."

As used herein, the term "candidate GABA analog" refers to any compound that may have the property of being a GABA analog.

As used herein, the term "GABA transaminase inhibitor" refers to a chemical or other substance capable of inhibiting the activity of an enzyme (e.g., a transaminase) that normally acts to transfer an amino group from GABA to an acceptor, or from an amino donor onto an acceptor, thus forming GABA.

As used herein, the term "candidate GABA transaminase inhibitor" refers to any compound that may have the property of being a GABA transaminase inhibitor.

As used herein, the term "GABA inhibitor" refers to any chemical or other substance that acts to counteract the natural activity of GABA. Inhibitors may chemically resemble GABA or may differ in structure. The inhibitors may act by competitively interfering with GABA by binding to a target or may act by inhibiting the uptake of GABA into a plant. Another name often used to refer to such an inhibitor is an "antagonist."

As used herein, the term "candidate GABA inhibitor" refers to any compound that may have the property of being a GABA inhibitor.

As used herein, the term "modulator of GABA metabolism" refers to a compound capable of increasing or decreasing the cellular or tissue GABA levels of an organism.

As used herein, the term "monoecious" refers to plants having separate male and female flowers on the same plant. Maize (Zea mays), for example, has a tassel of male flowers at the top of the stalk and a group of female flowers (on the ear, or cob) lower down. A dioecious plant has male and female flowers on separate plants As used herein, the term "phenotype" refers to the detectable characteristics of a cell or organism, which characteristics are the manifestation of gene expression.

As used herein "POP2," refers to the plant locus corresponding to the nucleic acid sequence of GenBank accession no. AF351125 (SEQ ID NO: 1).

As used herein, the term "self-sterile" refers to a plant that is incapable of self-fertilization to yield viable progeny or that exhibits a substantially reduced ability to self-pollinate. A substantially reduced level of self-fertilization typically will mean a reduction in seed yield of at least 50%, but often even higher levels, such as 60, 70, 80, 90, or even 100%.

As used herein, the term "self-pollination" refers to the transfer of pollen from the anther to the stigma of the same plant.

As used herein, the term "transgene" refers to a genetic sequence which has been introduced into the genome of a plant by transformation.

VII. Examples

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

EXAMPLE 1

Defects in Pollen Tube Guidance Result in Sterility

Specific defects in pollen tube guidance were previously established as the basis for sterility in an *Arabidopsis* mutant that exhibited 300-fold reduction in seed production compared to wild type (Wilhelmi and Preuss, 1996). It was also shown that pollen tube guidance was the only apparent defect in this mutant plant; the pollen tubes did not adhere to pistil cells (funiculus of the ovule) and grew in random directions throughout the ovary instead of growing towards the normal target, the micropyle of the ovule (Wilhelmi and Preuss, 1996 and see also FIG. 1). In addition, it was determined that this mutant is self-sterile; the guidance defect only arises when male and female tissues carry the mutation.

Two genetic loci, designated pop2-1 and pop3-1, were previously believed necessary for sterility (Wilhelmi and Preuss, 1996). Pop2-1 had been mapped to chromosome 3 (FIG. 3) and pop3-1 was mapped to chromosome 5. However, a subsequent study by the inventors indicated that the pop2-1 locus alone was sufficient to render the plant sterile and that a closely segregating embryo lethal mutation resulted in the erroneous implication of the pop3-1 locus in sterility After identifying the pop2-1 defect (Laura Wilhelmi, Ph.D. thesis, University of Chicago), PCR primers were generated that amplified the DNA sequence at the site of the pop2 mutation. Subsequently, treating the PCR product with a restriction enzyme allowed the mutant and wild-type alleles to be unambiguously distinguished (Laura Wilhelmi, Ph.D. thesis, University of Chicago, 2000). Using this method, a reassessment of the genotypes of plants with segregating pop2 and pop3 alleles was carried out to clarify the complex genetic interactions between these genes.

Segregation of DNA polymorphisms in 110 sterile $F_2$ offspring from a wild type (Columbia ecotype) x sterile mutant (Landsberg ecotype) cross previously implicated two loci, pop2 and pop3, linked by 4.8 cM and 6 cM, respectively, to polymorphic markers. After cloning POP2, a pop2-1 dCAPS marker was designed and complete linkage (517 plants) to sterility was confirmed, as well as strong linkage (4.5 cM) to an embryo lethal (emb) lesion. Unexpectedly, rare pop2/POP2 plants lacking the emb mutation yielded fertile:sterile offspring in a 3:1 ratio (1144:340, P<0.01; $\chi^2$ test), suggesting a single gene trait. The previously observed bias for pop3 may therefore have resulted from the restoration of fitness of plants carrying emb or other lesions. Additional evidence indicates pop2-1 is sufficient for sterility: 1) analysis of molecular markers more closely linked to POP3 (within 2 cM) identified sterile pop2/pop2 plants that lacked the pop3 mutation (7 plants /110 total), 2) backcrosses of pop2/pop2, EMBI EMB plants to wild type yielded fertile:sterile F2 plants in a 3:1 ratio (1670:507, P<0.01; $\chi^2$ test), 3) copies of POP2 transgenes restored pop2-1 fertility, and 4) other pop2 alleles also cause sterility defects.

A. Identification of POP2 as an Omega Aminotransferases

The pop2-1 mutation was previously used to clone the POP2 gene by a map-based approach (Laura Wilhelmi, Ph.D. thesis, University of Chicago and FIG. 3). Upon transformation into pop2-1 mutant lines, the cloned gene was able to restore fertility. Based on protein homology searches, it was suggested at that time that POP2 might encode an aminotransferase, with highest homology to DAPA (Diamino Pelargonic acid) aminotransferases involved in biotin biosynthesis. However, subsequent protein sequence analysis involving updated genome sequence databases carried out by the inventors revealed that the POP2 protein sequence has an even greater homology to omega aminotransferases (FIG. 4). As shown in FIG. 4, the analysis program indicated that POP2 is more closely related to a β-alanine aminotransferase than to the DAPA category. Omega aminotransferases are involved in the biosynthesis and catabolism of omega amino acids such as β-alanine, ornithine and GABA (Gamma amino butyric acid).

The results revealed a significant ($P<1\times10^{-93}$) similarity to class III omega aminotransferases. This class of aminotransferases constitutes a large family with a conserved motif. Phylogenetic analysis showed that POP2 is most similar to the Pseudomonas β-alanine pyruvate amino transferase. The database contains close relatives of POP2 in tomato and pepper, suggesting that this enzyme is broadly conserved among plants. The Pseudomonas amino transferase is unusual in that it recognizes an omega amino acid, a group of amino acids that includes β-alanine, ornithine and GABA.

B. Accumulation of GABA in pop2 Sterile Flowers

To determine which omega amino acids could be a substrate of POP2, the concentration of individual free amino acids in wild type and mutant flowers was determined using the commercially available services of the Molecular Structure Facility, University of California, Davis. For the analysis, between 0.1 and 1 gram of tissue was crushed in liquid nitrogen, and extracted in 2.5 ml of methanol (625 µl), chloroform (1.5 ml), and water (375 µl). The sample was centrifuged to separate the phases and the upper phase collected and dried under nitrogen gas. The dried material was resuspended in water and sent for analysis. The samples extracts were then analyzed on a Beckman Amino Acid Analyzer (Beckman Instruments).

The results of the analysis are given in Table1. As can be seen, GABA levels were 100 times higher in pop2-1 flowers compared to wild type flowers. The concentration of β-alanine was also slightly higher in pop2-1 flowers relative to wild type (5-fold). The experiment was repeated twice, yielding an average and standard deviation (Table 1). Within the margin of error, no other amino acids showed a variation of more than two fold between the wild type and pop2-1 flowers. Genetic analysis indicated that the pop2-1 mutation causes a loss of function of the POP2 gene. Therefore, the significant increase of GABA levels in pop2-1 flowers suggests that the normal function of POP2 is in GABA catabolism. Biochemical pathways involving GABA, called the GABA shunt, have been previously elucidated in other organisms (see, e.g., Shelp et al., 1999; FIG. 5). In this pathway, glutamate is converted to GABA which is then broken down to succinic semialdehyde by GABA transaminase. Succinic semialdehyde is then converted to succinate before it enters the KREB's cycle or to 4-hydroxybutyrate. Based on sequence homology to a transaminase and the accumulation of GABA in the pop2-1 mutant (Table 1), it was concluded that POP2 encodes a GABA transaminase in *Arabidopsis* (FIG. 6).

C. Increased GABA Levels Correlate with Decreased Fertility

Wild type *Arabidopsis* plants exhibit limited branching in their inflorescence stems. In contrast, pop2-1 sterile plants have extensive branching, typical of many sterile plants. In pop2-1, siliques (fruits) in the secondary branches have more seeds than those in the primary branch (FIG. 6B). To investigate whether this difference in fertility also correlated with GABA levels in the flowers of the primary and secondary branches, total amino acids were quantified from flowers isolated separately from these two types of branches. Amino acid analysis was performed as described above using the service commercially available from the University of California, Davis. A primary branch is the first inflorescence that arises from the rosette of leaves of a young Arabidopsis plant. A secondary branch is a branch that arises later than the first inflorescence and also initiates at a meristem that resides on the first inflorescence. Fertility in these branches was measured by opening developing siliques and counting the number of seeds. As shown in FIG. 6A, it was found that GABA levels remained the same in primary and secondary branch flowers of wild type plants. In pop2-1, a significant decrease in GABA levels was found in secondary branch flowers, which showed increased fertility compared to primary branch flowers. The concentration of all other amino acids remained the same in pop2-1 primary and secondary branch flowers. These results indicated that increased GABA levels correlate with decreased fertility.

To confirm the relationship between the GABA levels and fertility, additional plants were isolated with mutations in the POP2 gene PCR primers corresponding to the POP2 gene were used to screen a library of plants containing T-DNA insertions, using the commercial facility at the University of Madison, Madison, Wis. (see www.biotech.wisc.edu/Arabidopsis/). PCR products were amplified with one primer corresponding to the POP2 gene and a second primer corresponding to the T-DNA. Genomic DNA from pools of T-DNA mutants was amplified, and pools that yielded a PCR product (and thus had a T-DNA insert near the POP2 gene) were detected by Southern hybridization, using the POP2 gene as a probe. Subsequent screening of subpools was also performed by the Madison facility. After a small pool of plants with an insertion near POP2 was identified, individual plants were grown and used for PCR. DNA sequencing of the PCR products indicated the site of the inserted T-DNA. Two additional mutant lines were identified with insertions of transfer DNA (T-DNA) into the pop2 gene (Krysan et al., 1999). Flowers isolated from two of these lines (pop2-2 and pop2-3) exhibited an increase in GABA levels relative to the wild type flowers (FIG. 7). Interestingly, the increase in these two lines was less than in pop2-1 flowers.

To demonstrate that samples were equally loaded, duplicate dot blots were probed with antibodies raised against glutamate and they did not show similar variation among these lines (FIG. 7). Dot blots were performed by spotting an extract from flowers onto a nitrocellulose filter. To make the extract, between 0.1 and 1 gram of tissue was crushed in liquid nitrogen and extracted in 2.5 ml of methanol (625 µl), chloroform (1.5 ml), and water (375 µl). The sample was centrifuged to separate the phases and the upper phase was collected and dried under nitrogen gas. The dried material was resuspended in water. The suspended material was conjugated to 1% bovine serum albumin (BSA) in 2.5% glutaraldehyde at room temperature for at least 12 hours. The suspension was spotted onto a nitrocellulose filter either as a concentrate or in serial dilutions.

The filter was incubated at room temperature for 30 min in blocking buffer (5% nonfat dried milk in Tris Saline buffer (20 mM Tris, 136 mM NaCl, 0.1% Tween 20, pH 7.5) and then for 1 hour at room temperature in the same buffer, but with the addition of antibodies against glutamate or GABA (Sigma catalog #G2982 and #A2052, respectively). The antibodies were diluted as the manufacturer recommended (1:1000 dilution from the concentrated stock). Next, the filter was washed three times at room temperature in Tris Saline buffer. Following the wash, a secondary antibody (rabbit anti-mouse, IgG, conjugated to horseradish peroxidase, Pierce, catalog #31450) was added at 1:5000 and incubated for 30 min at room temperature in Tris Saline buffer. Detection of bound antibodies was performed using an ECL kit (Amersham Life Science, catalog #1059243 and #1059250) according to the manufacturers instructions. The resulting chemiluminescent signal was detected on X-ray film.

D. Localization of GABA

To further understand the functional significance of GABA accumulation, further studies were carried out to identify the organs of pop2-1 plants in which GABA levels were significantly increased relative to the wild type. Total amino acids were isolated from leaves, pollen and ovules of wild type and pop2-1 plants. Dot blots containing these extracts were probed with antibodies raised against GABA or glutamate (see above). As shown in FIG. 8, the GABA levels in pop2-1 leaves was lower than that found in pop2-1 ovules or pollen, although it was higher than the levels in wild type leaves. The GABA levels were higher in pop2-1 pollen and ovules compared to the corresponding wild type organs. The increased accumulation observed in male (pollen) and female (ovule) tissues is consistent with the self-sterile phenotype of pop2-1 flowers.

Figure 1:
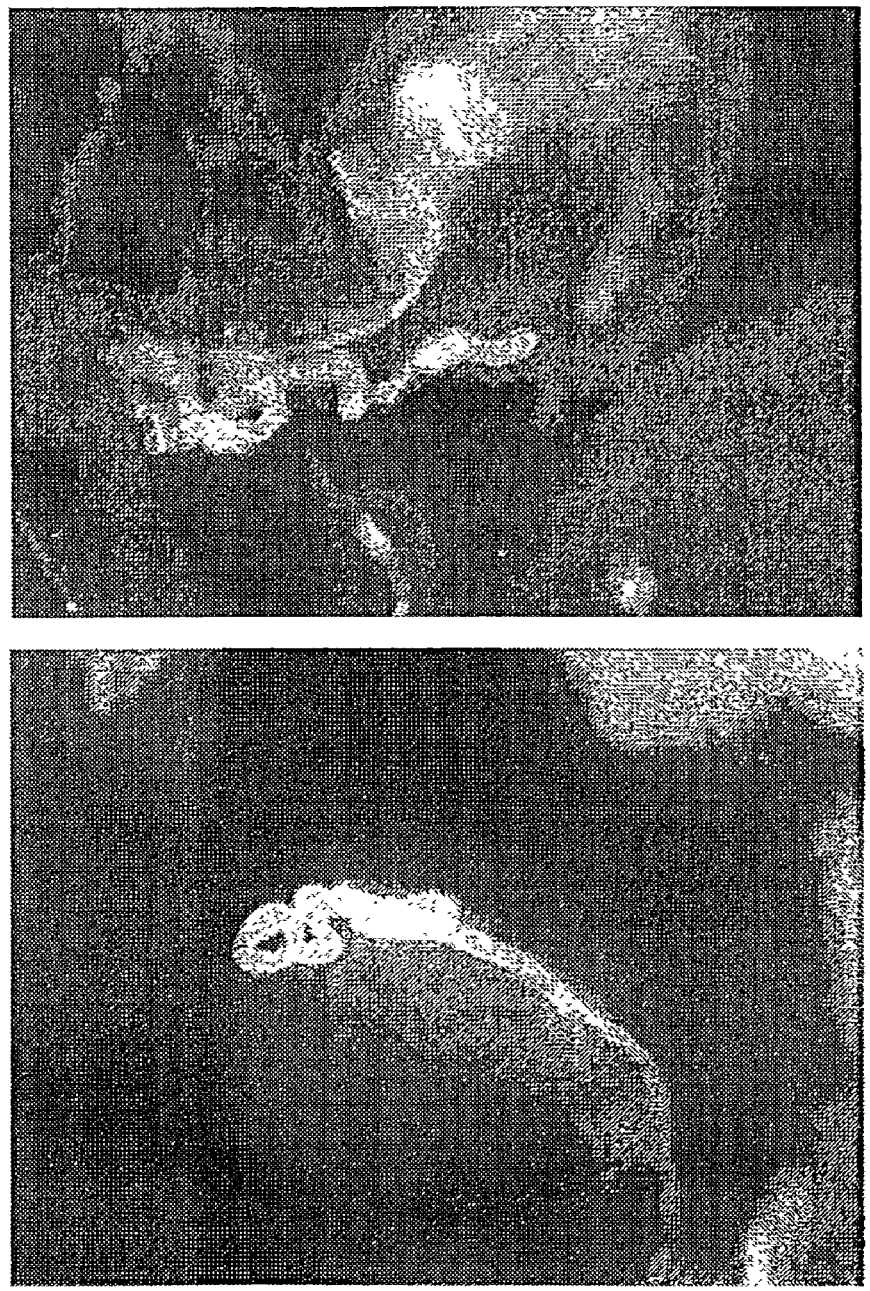
FIGS. 1A and B: Pollen tube guidance defects in pop2 mutant. The pollen tube shows growth in random directions throughout the ovary instead of growth towards the normal target, the micropyle of the ovule (Wilhelmi and Preuss, 1996).
Figure 2:
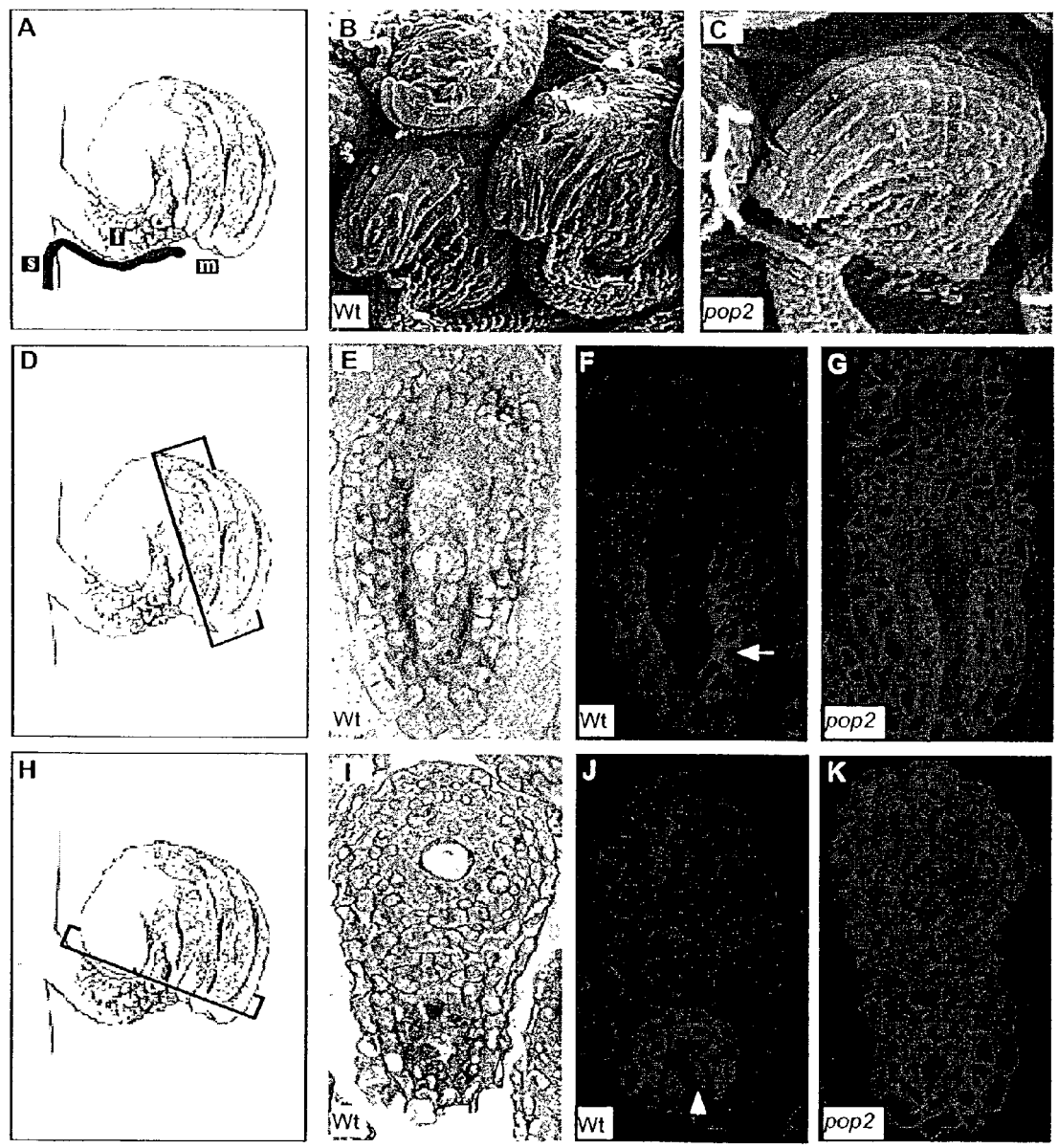
FIG. 2: GABA localization in ovules.

To further understand the role of GABA in pollen tube guidance, cell-specific localization of GABA was performed within pistils. Thin sections of pollinated wild type or pop2-1 pistils were made and probed with anti-GABA antibodies (FIG. 1 and FIG. 10).

Pistils were pollinated and fixed in 2.5% glutaraldehyde (Polysciences), 4% formaldehyde (Fisher) in PBS, phosphate buffered saline (10 mM potassium phosphate, 145 mM sodium chloride, pH 8.0). Fixed samples were washed three times in PBS and incubated in an ethanol series (50%, 70%, 85%, 95%, and 100%) at room temperature. Each incubation was for 15 minutes and was repeated once. Samples were washed three times in room-temperature 100% ethanol for 15 minutes each, washed twice in butanol:ethanol (50% : 50%, vol:vol) for 15 min, and washed twice in 100% butanol for 2 hours each. Samples were infiltrated in molten paraffin (Fisher) for 48 hours at 55° C.; fresh paraffin was added and another incubation of 24 hours was performed, also at 55° C.

After polymerization, 10 μm sections were cut on a Spencer-Lens Co. (Buffalo, N.Y.) ultramicrotome and probed with anti-GABA antibodies. In situ antibody staining was performed by exposing the plant tissue to blocking buffer (5% bovine serum albumin in PBS) for 30 min at room temperature, and then overnight at 4° C. in the same buffer, but with the addition of antibodies against GABA (Sigma catalog # A2052). The antibodies were diluted 1:100 from the concentrated stock. Next, the tissue was washed three times at room temperature in PBS. Following the wash, a secondary antibody (rabbit anti-mouse, IgG, conjugated to 1 nm gold particles, Amersham Life Science, catalog #RPN471) was added at 1:200 and incubated for 30 min at room temperature in PBS. Detection of bound antibodies was performed using an IntenSE™M silver enhancement kit (Amersham Life Science, catalog #RPN491) according to the manufacturers instructions. The resulting stain was observed by light microscopy.

Consistent with the GABA quantification and dot blot results described earlier, pop2-1 pistils showed increased accumulation of GABA relative to the wild type pistils (FIG. 10). The pistils used in these experiments had been pollinated and therefore contained pollen tubes that had traveled through them and fertilized ovules. To investigate if there is any specific localization of GABA in the path that the pollen tube takes to the ovules, similar studies are being carried out with unpollinated pistils.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

WO0061763
Devlin, *J Exp Biol.*, 204(Pt 5):887–96, 2001.
Enna, *Biochem. Pharmacol.*, 30, 907–15, 1983.
Gerasimov et al., *Eur J Pharmacol.*, 395(2):129–35, 2000.
Iversen, *Mol Psychiatry.*, 5(4):357–62, 2000.
Jefferson, *J Clin Psychiatry.*, 62 Suppl 1:50–3, 2001.
Johannessen, *Neurochem Int.*, 37(2–3):103–10, 2000.
Krogsgaard-Larsen et al., *Curr Pharm Des.*, 6(12):1193–209, 2000.
Krogsgaard-Larsen et al., *Medical Res. Reviews*, 1:27–56, 1988.
Krysan et al., *Plant Cell.* 1999 December;11(12):2283–90, 1999.
Potschka et al., *Naunyn Schmiedebergs Arch Pharmacol.*, 361(2):200–5., 2000.
Rebak et al., *Science*, 205, 211–13., 1979
Schousboe *Neurochem Res.*, 25(9–10):1241–4, 2000.
Schwartz, *Biochem. Pharmacol.* 27, 3369–76, 1988.
Shelp et al., *Trends Plant Sci.*, 4(11):446–452, 1999.
Silverman et al., *J. Med. Chem.*, 29:1840–1846, 1986
Silverman et al., *J. Med. Chem.*, 29:764–770, 1986.
Silverman et al., *Life Sci.*, 32:2717–2723, 1983.
Thompson et al., *Nucleic Acids Res.*, 22:4673–4680, 1994.
Wilhelmi and Preuss, *Science.*, 274(5292):1535–7, 1996.
Wilhelmi, In: *The Arabidopsis POP2 and POP3 Genes: Key Components in Pollen Tube Guidance*, Ph.D. thesis, The University of Chicago, 1999.

What is claimed is:

1. A method of modulating the fertility of a plant comprising treating said plant with GABA or a GABA analog wherein said treating provides a source of GABA or the GABA analog to said plant during flowering.

2. The method of claim 1, wherein the GABA analog is selected from the group consisting of forskolin, gabapentin and pregabalin, 4-cis-aminocrotonic acid, 3-hydroxy-4-methylamino-4,5,6,7-tetrahydro-1,2-benzisoxazole (N-methyl-exo-THPO), Tetrahydroisoxazolo pyridin-3-ol (THIP), Imidazole acetic acid, Isoguvacine, Muscimol, Baclofen, Cis-aminocrotonic acid (CACA) and Transaminocrotonic acid (TACA).

3. The method of claim 1, wherein the plant is a monoecious plant.

4. The method of claim 3, further defined as a method of creating a male sterile plant, wherein treating said plant comprises treating the male portion of flowers on said plant.

5. The method of claim 1, wherein said modulating comprises rendering said plant-sterile.

6. The method of claim 5, wherein said modulating comprises rendering said plant self-sterile.

7. The method of claim 1, wherein the plant is a dicotyledonous plant.

8. The method of claim 7, wherein the dicotyledonous plant is selected from the group consisting of tobacco, tomato, potato, sugar beet, pea, carrot, cauliflower, broccoli, soybean, canola, sunflower, alfalfa, and cotton.

9. The method of claim 7, wherein the dicotyledonous plant is *Arabidopsis thaliana*.

10. The method of claim 1, wherein the plant is a monocotyledonous plant.

11. The method of claim 10, wherein said monocotyledonous plant is selected from the group consisting of wheat, maize, rye, rice, turfgass, oat, barley, sorghum, millet, and sugarcane.

12. The method of claim 1, wherein treating comprises treating a flower on the plant.

13. The method of claim 1, wherein treating comprises an over the top application of the GABA or GABA analog.

* * * * *